US006306590B1

(12) United States Patent
Mehta et al.

(10) Patent No.: US 6,306,590 B1
(45) Date of Patent: *Oct. 23, 2001

(54) MICROFLUIDIC MATRIX LOCALIZATION APPARATUS AND METHODS

(75) Inventors: Tammy Burd Mehta, San Jose; Anne R. Kopf-Sill, Portola Valley, both of CA (US)

(73) Assignee: Caliper Technologies Corp., Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/093,832

(22) Filed: Jun. 8, 1998

(51) Int. Cl.[7] .................................................. C12Q 1/68
(52) U.S. Cl. ........................... 435/6; 435/173.1; 435/814; 435/91.2; 422/68.1
(58) Field of Search .................... 422/50, 54, 55, 422/56, 57, 58, 68.1, 69, 82.02, 82.05–82.09, 129, 131; 435/91.2, 91.1, 6, 5, 291, 810, 90–91, 91.51, 91.5, 173.1, 174, 176–177, 283.1, 285.1–285.2, 287.1–287.3, 287.7–287.9, 808, 814; 436/22.1, 23.1, 25.1, 518, 524, 525, 528, 531–532, 63, 164–6, 169, 172, 175, 805

(56) References Cited

U.S. PATENT DOCUMENTS

| | | |
|---|---|---|
| 5,585,069 | * 12/1996 | Zanzucchi et al. . |
| 5,587,128 | * 12/1996 | Wilding et al. . |
| 5,699,157 | 12/1997 | Parce . |
| 5,716,825 | * 2/1998 | Hancock et al. . |
| 5,770,029 | * 6/1998 | Nelson et al. . |
| 5,779,868 | 7/1998 | Parce et al. . |
| 5,800,690 | 9/1998 | Chow et al. . |
| 5,842,787 | 12/1998 | Kopf-Sill et al. . |
| 5,852,495 | 12/1998 | Parce . |
| 5,869,004 | 2/1999 | Parce et al. . |
| 5,876,675 | 3/1999 | Kennedy . |
| 5,880,071 | 3/1999 | Parce et al. . |
| 5,882,465 | 3/1999 | McReynolds . |
| 5,885,470 | 3/1999 | Parce et al. . |
| 5,965,410 | * 10/1999 | Chow et al. . |
| 5,989,402 | * 11/1999 | Chow et al. . |
| 6,007,690 | * 12/1999 | Nelson et al. . |
| 6,013,166 | * 1/2000 | Heller . |

FOREIGN PATENT DOCUMENTS

| | | |
|---|---|---|
| WO 96/04547 | 2/1996 | (WO) . |
| WO 98/00231 | 1/1998 | (WO) . |
| WO 98/00705 | 1/1998 | (WO) . |
| WO 98/00707 | 1/1998 | (WO) . |
| WO 98/02728 | 1/1998 | (WO) . |
| WO 98/05424 | 2/1998 | (WO) . |
| WO 98/22811 | 5/1998 | (WO) . |
| WO 98/45481 | 10/1998 | (WO) . |
| WO 98/45929 | 10/1998 | (WO) . |
| WO 98/46438 | 10/1998 | (WO) . |
| WO 98/49548 | 11/1998 | (WO) . |

(List continued on next page.)

OTHER PUBLICATIONS

Effenhauser et al. (1994). High–speed separation of anti-sense oligonucleotides on a micromachined capillary electrophoresis device. Anal. Chem. 66:2949–2953.*

(List continued on next page.)

*Primary Examiner*—Long V. Le
*Assistant Examiner*—Minh-Quan K. Pham
(74) *Attorney, Agent, or Firm*—Gulshan H. Shaver; The Law Offices of Jonathan Alan Quine

(57) ABSTRACT

Multiphasic microfluidic apparatus for performing product fluid manipulation and separation in a single continuous unit are provided. Related methods, kits, and compositions are also provided.

19 Claims, 7 Drawing Sheets

FOREIGN PATENT DOCUMENTS

| | | |
|---|---|---|
| WO 98/55852 | 12/1998 | (WO) . |
| WO 98/56956 | 12/1998 | (WO) . |
| WO 99/00649 | 1/1999 | (WO) . |
| WO 99/10735 | 3/1999 | (WO) . |
| WO 99/12016 | 3/1999 | (WO) . |
| WO 99/16162 | 4/1999 | (WO) . |
| WO 99/19056 | 4/1999 | (WO) . |
| WO 99/19516 | 4/1999 | (WO) . |
| WO 99/29497 | 6/1999 | (WO) . |

OTHER PUBLICATIONS

Woolley et al. (1994). Ultra–high–speed DNA fragment separations using microfabricated capillary array electrophoresis chips. PNAS USA. 91:11348–11352.*

Wilding et al. (1994). PCR in a silicon microstructure. Clin. Chem. 40(9):1815–1818.*

Neckers, et al., (1989) Photopolymerization Using Derivatives of Fluorescent. *Polym. Material Sci. Eng.*, 60:15.

Fouassier, et al., (1991) Polymerisation induite sous irradiation laser visible. *Makromol. Chem.*, 192:245–260.

Beskin, et al. (1995) On the mechanism of the modular primer effect. *Nucleic Acids Research* 23(15):2881–2885.

Hagiwara, et al., (1996) Long distance sequencer' method; a novel strategy for large DNA sequencing projects. *Nucleic Acids Research* 24(12):2460–2461.

Porter et al. (1997) Direct PCR sequencing with boronated nucleotides. *Nucleic Acids Research* 25(8):1611–1617.

Raja et al. (1997) DNA sequencing using differential extension with nucleotide subsets (DENS). *Nucleic Acids Research* 25(4):800–805.

* cited by examiner

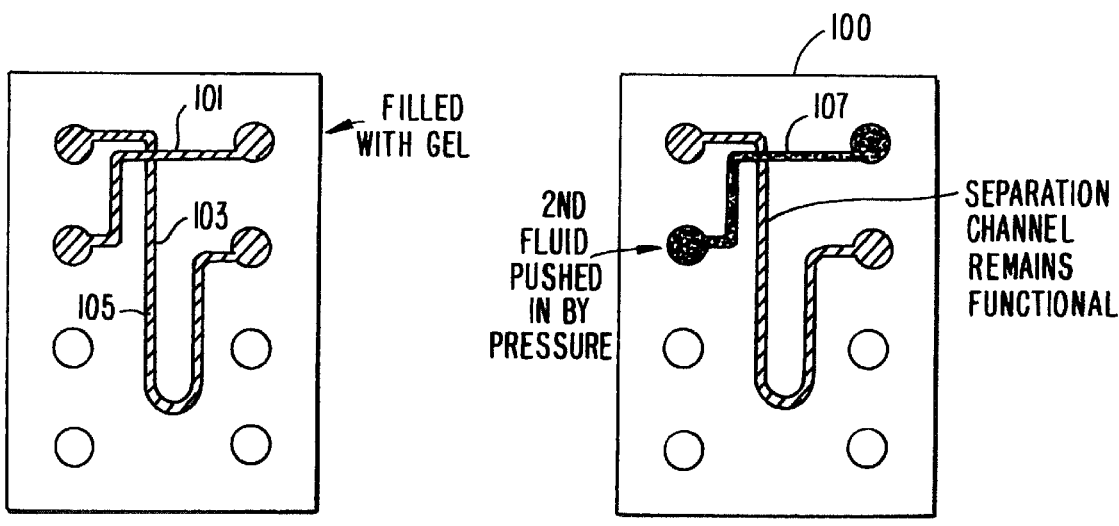
FIG. 1A.
FIG. 1B.
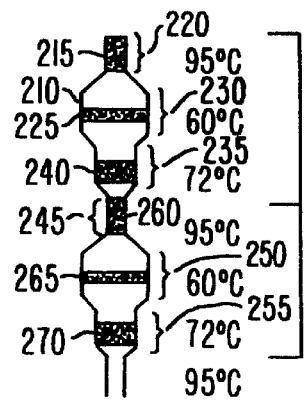
FIG. 2.

MICROFLUIDIC MATRIX LOCALIZATION APPARATUS AND METHODS

BACKGROUND OF THE INVENTION

Manipulating fluidic reagents and assessing the results of reagent interactions are central to chemical and biological science. Manipulations include mixing fluidic reagents, assaying products resulting from such mixtures, and separation or purification of products or reagents and the like. Assessing the results of reagent interactions can include autoradiography, spectroscopy, microscopy, photography, mass spectrometry, nuclear magnetic resonance and many other techniques for observing and recording the results of mixing reagents. A single experiment may involve literally hundreds of fluidic manipulations, product separations, result recording processes and data compilation and integration steps. Fluidic manipulations are performed using a wide variety of laboratory equipment, including various fluid heating devices, fluidic mixing devices, centrifugation equipment, molecule purification apparatus, chromatographic machinery, gel electrophoretic equipment and the like. The effects of mixing fluidic reagents are typically assessed by additional equipment relating to detection, visualization or recording of an event to be assayed, such as spectrophotometers, autoradiographic equipment, microscopes, gel scanners, computers and the like.

Because analysis of even simple chemical, biochemical, or biological phenomena requires many different types of laboratory equipment, the modern laboratory is complex, large and expensive. In addition, because so many different types of equipment are used in even conceptually simple experiments such as DNA synthesis or sequencing, it has not generally been practical to integrate different types of equipment to improve automation. The need for a laboratory worker to physically perform many aspects of laboratory science imposes sharp limits on the number of experiments which a laboratory can perform, and increases the undesirable exposure of laboratory workers to toxic or radioactive reagents.

One particularly labor intensive biochemical series of laboratory fluidic manipulations is nucleic acid synthesis and analysis. A variety of in vitro amplification methods for biochemical synthesis of nucleic acids are available, such as the polymerase chain reaction (PCR). See, Mullis et al., (1987) U.S. Pat. No. 4,683,202 and *PCR Protocols A Guide to Methods and Applications* (Innis et al. eds, Academic Press Inc. San Diego, Calif. (1990) (Innis). PCR methods typically require the use of specialized machinery for performing thermocycling reactions to perform DNA synthesis, followed by the use of specialized machinery for electrophoretic analysis of synthesized DNA. For a description of nucleic acid manipulation methods and apparatus see Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1997, supplement 37) (Ausubel).

Another particularly important and labor intensive biochemical series of laboratory fluidic manipulations which are typically performed on nucleic acids which are made recombinantly or synthetically is nucleic acid sequencing. Efficient DNA sequencing technology is central to the development of the biotechnology industry and basic biological research. Improvements in the efficiency and speed of DNA sequencing are needed to keep pace with the demands for DNA sequence information. The Human Genome Project, for example, has set a goal of dramatically increasing the efficiency, cost-effectiveness and throughput of DNA sequencing techniques. See, e.g., Collins, and Galas (1993) *Science* 262:43–46.

Most DNA sequencing today is carried out by chain termination methods of DNA sequencing. The most popular chain termination methods of DNA sequencing are variants of the dideoxynucleotide mediated chain termination method of Sanger. See, Sanger et al. (1977) *Proc. Nat. Acad. Sci., USA* 74:5463–5467. For a simple introduction to dideoxy sequencing, see, Ausubel or Sambrook, supra. Four color sequencing is described in U.S. Pat. No. 5,171,534. Thousands of laboratories employ dideoxynucleotide chain termination techniques. Commercial kits containing the reagents most typically used for these methods of DNA sequencing are available and widely used.

In addition to the Sanger methods of chain termination, new PCR exonuclease digestion methods have also been proposed for DNA sequencing. Direct sequencing of PCR generated amplicons by selectively incorporating boronated nuclease resistant nucleotides into the amplicons during PCR and digestion of the amplicons with a nuclease to produce sized template fragments has been proposed (Porter et al. (1997) *Nucleic Acids Research* 25(8):1611–1617). In the methods, 4 PCR reactions on a template are performed, in each of which one of the nucleotide triphosphates in the PCR reaction mixture is partially substituted with a 2'deoxynucleoside 5'-α[P-borano]-triphosphate. The boronated nucleotide is stocastically incorporated into PCR products at varying positions along the PCR amplicon in a nested set of PCR fragments of the template. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it requires fewer biochemical manipulations than performing standard Sanger-style sequencing of PCR amplicons.

Other sequencing methods which reduce the number of steps necessary for template preparation and primer selection have been developed. One proposed variation on sequencing technology involves the use of modular primers for use in PCR and DNA sequencing. For example, Ulanovsky and co-workers have described the mechanism of the modular primer effect (Beskin et al. (1995) *Nucleic Acids Research* 23(15):2881–2885) in which short primers of 5–6 nucleotides can specifically prime a template-dependent polymerase enzyme for template dependent nucleic acid synthesis. A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al. (1997) *Nucleic Acids Research* 25(4):800–805.

Improvements in methods for generating sequencing templates have also been developed. DNA sequencing typically involves three steps: i) making suitable templates for the regions to be sequenced (i.e., by synthesizing or cloning the nucleic acid to be sequenced); ii) running sequencing reactions for electrophoresis, and iii) assessing the results of the reaction. The latter steps are sometimes automated by use of large and very expensive workstations and autosequencers. The first step often requires careful experimental design and laborious DNA manipulation such as the construction of nested deletion mutants. See, Griffin, H. G. and Griffin, A. M. (1993) *DNA sequencing protocols,* Humana Press, New Jersey. Alternatively, random "shot-gun" sequencing methods, are sometimes used to make templates, in which randomly selected sub clones, which may or may not have overlapping sequence information, are randomly sequenced. The sequences of the sub clones are compiled to produce an ordered sequence. This procedure eliminates complicated DNA manipulations; however, the method is inherently inefficient because many recombinant clones must be sequenced due to the random nature of the procedure. Because of the labor intensive nature of sequencing, the repetitive sequencing of many individual clones dramatically reduces the throughput of these sequencing systems.

Recently, Hagiwara and Curtis (1996) *Nucleic Acids Research* 24(12):2460–2461 developed a "long distance sequencer" PCR protocol for generating overlapping nucleic acids from very large clones to facilitate sequencing, and methods of amplifying and tagging the overlapping nucleic acids into suitable sequencing templates. The methods can be used in conjunction with shotgun sequencing techniques to improve the efficiency of shotgun methods.

In an attempt to increase laboratory throughput and to decrease exposure of laboratory workers to reagents, various strategies have been performed. For example, robotic introduction of fluids onto microtiter plates is commonly performed to speed mixing of reagents and to enhance experimental throughput. More recently, microscale devices for high throughput mixing and assaying of small fluid volumes have been developed. For example, U.S. Pat. No. 6,046,056 provides pioneering technology related to microscale fluidic devices, especially including electrokinetic devices. The devices are generally suitable for assays relating to the interaction of biological and chemical species, including enzymes and substrates, ligands and ligand binders, receptors and ligands, antibodies and antibody ligands, as well as many other assays. Because the devices provide the ability to mix fluidic reagents and assay mixing results in a single continuous process, and because minute amounts of reagents can be assayed, these microscale devices represent a fundamental advance for laboratory science. Pioneering integrated systems for nucleic acid sequencing utilizing microfluidic fluid manipulation are described in, e.g., provisional patent application U.S. Ser. No. 60/068,311, entitled "Closed Loop Biochemical Analyzer" by Knapp, filed Dec. 19, 1997 and U.S. Pat. No. 6,235,471.

In the electrokinetic microscale devices and systems provided by Parce et al. and Knapp above, an appropriate fluid is flowed into a microchannel etched in a substrate having functional groups present at the surface. The groups ionize when the surface is contacted with an aqueous solution. For example, where the surface of the channel includes hydroxyl functional groups at the surface, e.g., as in glass substrates, protons can leave the surface of the channel and enter the fluid. Under such conditions, the surface possesses a net negative charge, whereas the fluid will possess an excess of protons, or positive charge, particularly localized near the interface between the channel surface and the fluid. By applying an electric field along the length of the channel, cations will flow toward the negative electrode. Movement of the sheath of positively charged species in the fluid pulls the solvent with them.

Although improvements in robotic manipulation of fluidic reagents and miniaturization of laboratory equipment have been made, and although particular biochemical processes such as DNA amplification and sequencing are very well developed, there still exists a need for additional techniques and apparatus for mixing and assaying fluidic reagents, for integration of such systems and for reduction of the number of manipulations required to perform biochemical manipulations such as DNA sequencing. Ideally, these new apparatus would be useful with, and compatible to, established biochemical protocols. This invention provides these and many other features.

SUMMARY OF THE INVENTION

The present invention provides multi-phasic microfluidic apparatus which are suitable for performing fluidic mixing followed by separation of mixing products. These apparatus have fluid mixing regions such as microfluidic channels and fluidly connected product separation regions, e.g., microchannels comprising a sieving matrix such as a separations gel. Thus, mixing reactions, including, e.g., PCR, can be performed in a first fluidic phase, followed by a separation reaction in a second fluidic separations phase. The fluid connection regions are typically unvalved, and/or electrically gated and optionally comprise electrical control elements.

Several techniques for making multi-phasic microfluidic apparatus are also provided. In one embodiment, a first phase such as a gel, is selectively cross-linked at regions of a microchannel where gel is desired (e.g. by photopolymerizing the gel in place). In other embodiments, pressure (negative or positive) is used to force one fluidic phase into a specified portion of a microchannel. Different fluidic phases are optionally loaded electrokinetically. Other techniques are also shown.

In operation, components are typically made or purified in a first phase (e.g., a PCR amplification mixture, DNA sequencing reaction, binding reaction, enzyme reaction, or the like) and separated in a second phase such as a sieving matrix. In a preferred embodiment, products produced in the first phase are electrically loaded on the second phase, where the components initially stack and then separate as they electrophorese through the second phase.

In addition, it is surprisingly discovered that the PCR reaction can be performed in the presence of a variety of sieving matrices, including: agarose, linear polyacrylamide, methylcellulose, polyethylene oxide and hydroxy ethyl cellulose and that resulting PCR products are separable in the microfluidic devices herein. Accordingly, elegant chip designs for performing PCR in microfluidic chips are shown for mixing PCR reaction components and sieving matrixes, performing thermocycling reactions and separating resulting PCR products in microfluidic channels.

BRIEF SUMMARY OF THE FIGURES

FIGS. 1A–1B is a schematic drawing of the "12 A" chip.

FIG. 2 is a schematic drawing of a microchannel for joule heating.

DETAILED DESCRIPTION OF THE INVENTION

Figure 3B:
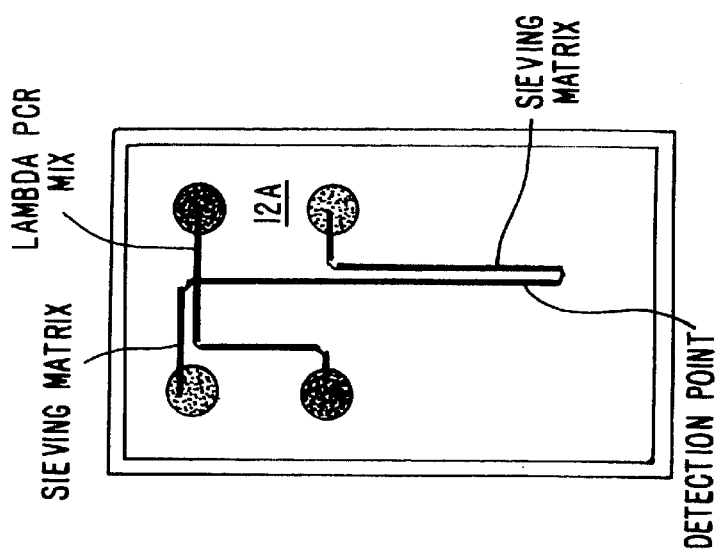
FIG. 3B is a schematic drawing of the 12 A chip.

Many laboratory fluidic operations are highly cumbersome, requiring many steps and a high labor input. This high labor input makes the efficiency of the modern laboratory relatively low compared to many manufacturing or service industries. Accordingly, extensive attempts to improve efficiency for laboratory fluidic operations have been made, utilizing robotics and miniaturization. Most recently, microfluidic operations using electrokinetic microfluidic apparatus have revolutionized laboratory operations. See, e.g., International Patent Application No. WO 96/04,547 to Ramsey et al., as well as U.S. Patents 6,046,056 and 60/976,336, and USSN 60/068,311, by Knapp and USSN 60/086,240 by Knapps et al.

The invention provides apparatus and related kits, methods of making the apparatus and kits and methods of using the apparatus and kits. These apparatus and related methods provide multi-phasic microfluidic apparatus suitable for performing integrated fluidic operations. Using the apparatus and methods, it is possible to perform many or all of the fluidic operations needed for an experiment or diagnostic procedure in an integrated fashion in a single apparatus. The present invention provides apparatus, systems and methods for dramatically increasing the speed and simplicity of screening, manipulating and assessing fluidic reagents, reagent mixtures, reaction products (including the products of DNA sequencing reactions) and the like. The invention provides integrated systems for performing a variety of chemical, biochemical and biological experiments and other fluidic operations, including PCR, DNA sequencing, integrated or sequential screening of chemical or biological libraries, and the like. Although the microfluidic systems of the invention are generally described in terms of the performance of chemical, biochemical or biological reactions separations, incubations and the like, it will be understood that, as fluidic systems having general applicability, these systems can have a wide variety of different uses, e.g., as metering or dispensing systems in both biological and nonbiological applications.

Making Multi-Phasic Microfluidic Apparatus

The apparatus of the invention are typically "multi-phasic," although uniphasic embodiments, particularly for PCR amplification, are also contemplated. The phrase "multi-phasic" is intended to indicate a microfluidic apparatus which includes microchannels, microchambers, microwells or the like, where there are at least two different fluidic phases present in the apparatus. For example, in one embodiment, crossing microchannels comprise different fluidic phases. For example, a first fluidic phase (e.g., a biological or chemical reaction mixture) in a first microchannel can cross a second microchannel comprising a second fluidic phase (e.g., a sieving matrix) adapted to analyzing components of the first fluidic phase.

An example simple apparatus of the invention is provided by FIG. 1. Fluidic reaction channel 101 and fluidic separations channel 103 are filled with separation matrix 105 which can be any separations matrix as described more fully below, including a polyacrylamide gel or solution. Separation matrix 105 is replaced in fluidic channel 101, e.g., by flowing buffer 107 into fluidic reaction channel 101 under pressure, thereby forcing separation matrix 105 out of channel 101. A variety of variations on this apparatus are discussed herein.

Making Microfluidic Substrates

The microfluidic devices of the invention typically comprise a substrate or body having microfluidic channels, chambers, wells or the like disposed therein, e.g., as depicted in FIG. 1. In the apparatus of the invention, at least two different fluid phases are also disposed within the substrate, e.g., in a plurality of reaction channels.

Manufacturing of microscale elements into the surface of substrates is generally carried out by any number of micro-fabrication techniques that are known in the art. For example, lithographic techniques are employed in fabricating, e.g., glass, quartz or silicon substrates, using methods, well known in the semiconductor manufacturing industries such as photolithographic etching, plasma etching or wet chemical etching. See, Sorab K. Gandhi, VLSI Principles: Silicon and Gallium Arsenide, NY, Wiley (see esp. Chapter 10). Alternatively, micromachining methods such as laser drilling, air abrasion, micromilling and the like are employed. Similarly, for polymeric substrates, well know manufacturing techniques are used. These techniques include injection molding or stamp molding methods where larage numbers of substrate are produced using e.g., rolling stamps to produce large sheets of microscale substrates or polymer microcasting techniques where the substrate is polymerized within a micromachined mold. Polymeric substrates are further described in Provisional Patent Application Ser. No. 60/015,498, filed Apr. 16, 1996 and U.S. Pat. 5,885,470.

In addition to micromachining methods, printing methods are also used to fabricate chambers channels and other microfluidic elements on a solid substrate. Such methods are taught in detail in U.S. Pat. No. 6,074,725. In brief, printing methods such as ink-jet printing, laser printing or other prining methods are used to print the outlines of a microfluidic element on a substrate, and a cover layer is fixed over the printed outline to provide a closed micrfluidic element.

The substrates of the invention optionally include a planar element which overlays the channeled portion of the substrate, enclosing and fluidly sealing the various channels, wells and other microfluidic elements. Attaching the planar cover element is achieved by a variety of means, including, e.g., thermal bonding, adhesives or, in the case of certain substrates, e.g., glass, or semi-rigid and non-rigid polymeric substrates, a natural adhesion between the two components. The planar cover element can additionally be provided with access ports and/or reservoirs for introducing the various fluid elements needed for a particular screen, and for introducing electrodes for electrokinetic movement.

Typically, an individual microfluidic device will have an overall size that is fairly small. Generally, the devices will have a square or rectangular shape, but the specific shape of the device can be easily varied to accommodate the users needs. While the size of the device is generally dictated by the number of operations performed within a single device, such devices will typically be from about 1 to about 20 cm across, and from about 0.01 to about 1.0 cm thick. In a preferred aspect, the devices include glass substrates with channels or other microfluidic elements fabricated therein or thereon. These substrates are typically easy to produce, making them potentially disposable.

Although microfabricated fluid pumping and valving systems are readily employed in the devices of the invention, the cost and complexity associated with their manufacture and operation can generally prohibit their use inmass-produced and potentially disposable devices as are envisioned by the present invention. The devices of the invention will typically include an electroosmotic fluid direction system. Such fluid direction systems combine the elegance of a fluid direction system devoid of moving parts, with an ease of manufacturing, fluid control and disposablity. Examples of particularly preferred electroosmotic fluid direction systems include, e.g., those described in International Patent Application No. WO 96/04,547 to Ramsey et al., as well as U.S. Pat. Nos. 6,046,056 and 5,976,336.

In brief, these fluidic control systems typically include electrodes disposed within reservoirs that are placed in fluid connection with the channels fabricated into the surface of the substrate. The materials stored in the reservoirs are transported through the channel system delivering appropriate volumes of the various materials to one or more regions on the substrate in order to carry out a desired screening assay.

Material transport and direction is accomplished through electrokinesis, e.g., electroosmosis or electrophoresis. As used herein, "electrokinetic material transport systems" or "electrokinetic devices" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode. Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures.

In brief, when an appropriate fluid is placed in a channel or other fluid conduit having functional groups present at the surface, those groups can ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them. An electrokinetic device moves components by applying an electric field to the components, typically in a microfluidic channel. By applying an electric field along the length of the channel, cations will flow toward a negative electrode, while anions will flow towards a positive electrode. Movement of charged species in the fluid pulls the solvent with the fluid. The steady state velocity of this fluid movement is generally given by the equation:

$$v = \frac{\epsilon \xi E}{4\pi \eta}$$

where v is the solvent velocity, $\epsilon$ is the dielectric constant of the fluid, $\xi$ is the zeta potential of the surface, E is the electric field strength, and $\eta$ is the solvent viscosity. The solvent velocity is, therefore, directly proportional to the surface potential.

To provide appropriate electric fields, the system generally includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple, independent voltage sources are used. The voltage controller is electrically connected to each of the reservoirs via an electrode positioned or fabricated within each of the plurality of reservoirs. In one embodiment, multiple electrodes are positioned to provide for switching of the electric field direction in a microchannel, thereby causing the analytes to travel a longer distance than the physical length of the microchannel. Use of electrokinetic transport to control material movement in interconnected channel structures was described in WO 96/04547 to Ramsey, which is incorporated by reference.

Substrate materials are also selected pro produce channels having a desired surface charge. In the case of glass substrates, the etched channels will possess a net negative charge resulting from the iodized hydroxyls naturally present at the surface. Alternatively, surface modifications are employed to provide an appropriate surface charge, e.g., coatings, derivatizations, e.g., silanation, or impregnation or the surface to provide appropriately charged groups on the surface. Examples of such treatments are described in, e.g., Provisional Patent Application Ser. No. 60/015,498, filed Apr. 16, 1996. See also, U.S. Pat. No. 5,885,470.

Modulating voltages are then concomitantly applied to the various reservoirs to affect a desired fluid flow characteristic, e.g., continuous or discontinuous (e.g., a regularly pulsed field causing the flow to oscillate direction of travel) flow of receptor/enzyme, ligand/substrate toward the waste reservoir with the periodic introduction of test compounds. Particularly, modulation of the voltages applied at the various reservoirs can move and direct fluid flow through the interconnected channel structure of the device in a controlled manner to effect the fluid flow for the desired screening assay and apparatus.

While a number of devices for carrying out particular methods according to the invention are described in substantial detail herein, it will be recognized that the specific configuration of these devices will generally vary depending upon the type of manipulation or reaction to be performed. The small scale, integratability and self-contained nature of these devices allows for virtually any reaction orientation to be realized within the context of the microlaboratory system.

Because the microfluidic devices of the invention preferably employ electroosmotic fluid direction systems, and are substantially sealed to the outside environment, excepting reagent, buffer or sample ports, they are capable of performing fluidic operations while maintaining precise control of the amounts of different fluids to be delivered to the different regions of the substrate.

Adding Multiple Phases to Microfluidic Substrates

One aspect of the invention is the placement of different fluidic phases in different regions of a microfluidic substrate. For example, it is advantageous to provide a microfluidic substrate with reaction components in one region and sieving matrix in other portions for the separation of reaction components. Accordingly, one aspect of the invention is the selective placement of fluidic phases in selected channels or channel regions of a microfluidic substrate. These materials (or precursors of the materials, e.g., monomers to be polymerized in subsequent steps as discussed below) are loaded into microfluidic components by electrokinesis or by pressurized pumping.

A wide variety of sieving and molecular partition matrixes are available, and can be used in the multi-phasic apparatus of the invention. For example, a variety of sieving matrixes, partition matrixes and the like are available from Supelco, Inc. (Bellefonte, Pa.; see, 1997 Suppleco catalogue). Common matrixes which are useful in the present invention include those generally used in low pressure liquid chromatography, gel electrophoresis and other liquid phase separations; matrix materials designed primarily for non-liquid phase chromatography are also useful in certain contexts, as the materials often retain separatory characteristics when suspended in fluids. For a discussion of electrophoresis see, e.g., Weiss (1995) *Ion Chromatography* VCH Publishers Inc.; Baker (1995) *Capillary Electrophoresis* John Wiley and Sons; Kuhn (1993) *Capillary Electrophoresis: Principles and Practice* Springer Verlag; Righetti (1996) *Capillary Electrophoresis in Analytical Biotechnology* CRC Press; Hill (1992) *Detectors for Capillary Chromatography* John Wiley and Sons; *Gel Filtration: Principles and Methods* (5th Edition) Pharmacia; Gooding and Regnier (1990) *HPLC of Biological Macromolecules: Methods and Applications* (Chrom. Sci. Series, volume 51) Marcel Dekker and Scott (1995) *Techniques and Practices of Chromatography* Marcel Dekker, Inc.

Commercially available low pressure liquid chromatography media include, e.g., non-ionic macroreticular and macroporous resins which adsorb and release components based upon hydrophilic or hydrophobic interactions such as Amberchrom resins (highly cross-linked styrene/divinylbenzene copolymers suitable for separation of peptides, proteins, nucleic acids, antibiotics, phytopharmacologicals, and vitamins); the related Amberlite XAD series resins (polyaromatics and acrylic esters) and amberchroms (polyaromatic and polymethacrylates) (manufactured by Rohm and Haas, available through Suppleco); Diaion (polyaromatic or polymethacrylic beads); Dowex (polyaromatics or substituted hydrophilic functionalized polyaromatics) (manufactured by Dow Chemical, available through Suppleco); Duolite (phenol-formaldehyde with methanolic functionality), MCI GEL sephabeads, supelite DAX-8 (acrylic ester) and Supplepak (polyaromatic) (all of the preceding materials are available from Suppleco). For a description of uses for Amberlite and Duolite resins, see, *Amberlite/Duolite Anion Exchange Resins* (Avaliable from Suppleco, Cat No. T412141). Gel filtration chromatography matrixes are also suitable, including sephacryl, sephadex, sepharose, superdex, superose, toyopearl, agarose, cellulose, dextrans, mixed bead resins, polystyrene, nuclear resins, DEAE cellulose, Benzyl DEA cellulose, TEAE cellulose, and the like (Suppleco).

Gel electrophoresis media include silica gels such as Davisil Silica, E. Merck Silica Gel, Sigma-Aldrich Silica Gel (all available from Suppleco) in addition to a wide range of silica gels available for various purposes as described in the Aldrich catalogue/handbook (Aldrich Chemical Company (Milwaukee, Wis.)). Preferred gel materials include agarose based gels, various forms of acrylamide based gels (reagents available from, e.g., Suppleco, SIGMA, Aldrich, SIGMA-Aldrich and many other sources) colloidial solutions such as protein colloids (gelatins) and hydrated starches. Various forms of gels are discussed further below.

A variety of affinity media for purification and separation of molecular components are also available, including a variety of modified silica gels available from SIGMA, Aldrich and SIGMA-Aldrich, as well as Suppleco, such as acrylic beads, agarose beads, cellulose, sepharose, sepharose CL, toyopearl or the like chemically linked to an affinity ligand such as a biological molecule. A wide variety of activated matrixes, amino acid resins, avidin and biotin resins, carbohydrate resins, dye resins, glutathione resins, hydrophobic resins, immunochemical resins, lectin resins, nucleotide/coenzyme resins, nucleic acid resins, and specialty resins are available, e.g., from Suppleco, SIGMA, Aldrich or the like. See also, Hermanson et al. (1992) *Immobilized Affinity Ligand Techniques* Academic Press.

Other media commonly used in chromatography are also adaptable to the present invention, including activated aluminas, carbopacks, carbosieves, carbowaxes, chromosils, DEGS, Dexsil, Durapak, Molecular Sieve, OV phases, pourous silica, chromosorb series packs, HayeSep series, Porapak series, SE-30, Silica Gel, SP-1000, SP-1200, SP-2100, SP-2250, SP-2300, SP2401, Tenax, TCEP, supelcosil LC-18-S and LC-18-T, Methacrylate/DVBm, polyvinylalcohols, napthylureas, non-polar methyl silicone, methylpolysiloxane, poly (ethylene glycol) biscyanopropyl polysiloxane and the like.

Several methods of providing fluidic regions in selected regions of a channel, or selected channels are provided. In a first aspect, multiple microfluidic regions are filled with a first fluid such as an unpolymerized solution that, upon polymerization, forms a sieving matrix. Elements of the microfluidic device such as microfluidic channels are filled with the first fluid by forcing the fluid into the channel under pressure, or by moving the fluid into the channel electrokinetically. In one embodiment, the first fluid polymerizes upon exposure to light (i.e., the fluid comprises a "photopolymerizable" polymer). The fluid is then selectively exposed to light (e.g., using photomasking techniques) in those regions where a polymerized gel is desired. Unpolymerized fluid is then optionally washed out of the unselected regions of the microfluidic device, or into a waste reservoir using electrokinetic flow or pressure.

A wide variety of free-radically polymerizable monomers photopolymerize to form gels, or can be made photopolymerizeable by the addition of, e.g., energy transfer dyes. For example, free-radically polymerizable monomers can be selected from acrylate, methacrylate and vinyl ester functionalized materials. They can be monomers and/or oligomers such as (meth)acrylates (meth)acrylamides, acrylamides, vinyl pyrrolidone and azalactones. Such monomers include mono-, di-, or poly-acrylates and methacrylates such as methyl acrylate, methyl methacrylate, ethyl acrylate, isopropyl methacrylate, isooctyl acrylate, isobornyl acrylate, isobornyl methacrylate, acrylic acid, n-hexyl acrylate, stearyl acrylate, allyl acrylate, glycerol diacrylate, glycerol triacrylate, ethylene glycol diacrylate, diethyleneglycol diacrylate, triethyleneglycol dimethacrylate, 1,6-hexanediol diacrylate, 1,3-propanediol diacrylate, 1,3-propanediol dimethacrylate, trimethanol triacrylate, 1,2,4-butanetriol trimethylacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl-dimethylmethane, bis[1-(3-acryloxy-2-hydroxy)]-propoxyphenyl dimethylmethane, tris-hydroxyethyl isocyanurate trimethacrylate; the bis-acrylates and bis-methacrylates of polyethylene glycols of molecular weight 200–500, copolymerizable mixtures of acrylated monomers, acrylated oligomers, PEG diacrylates, etc. Strongly polar monomers such as acrylic acid, acrylamide, itaconic acid, hydroxyalkyl acrylates, or substituted acrylamides or moderately polar monomers such as N-vinyl-2-pyrrolidone, N-vinyl caprolactam, and acrylonitrile are useful.

Proteins such as gelatin, collagen, elastin, zein, and albumin, whether produced from natural or recombinant sources, which are made free-radical polymerization by the addition of carbon-carbon double or triple bond-containing moieties, including acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups, can also be used to form sieving matrixes.

Dye-sensitized polymerization is well known in the chemical literature. For example, light from an argon ion laser (514 nm), in the presence of an xanthin dye and an electron donor, such as triethanolamine, to catalyze initiation, serves to induce a free radical polymerization of acrylic groups in a reaction mixture (Neckers, et al., (1989) *Polym. Materials Sci. Eng.*, 60:15; Fouassier, et al., (1991) *Makromol. Chem.*, 192:245–260). After absorbing laser light, the dye is excited to a triplet state. The triplet state reacts with a tertiary amine such as the triethanolamine, producing a free radical which initiates a polymerization reaction. Polymerization is extremely rapid and is dependent on the functionality of the composition, its concentration, light intensity, and the concentration of dye and, e.g., amine.

Dyes can be used which absorb light having a frequency between 320 nm and 900 nm, can form free radicals, are water soluble, etc. There are a large number of photosensitive dyes that can be used to optically initiate polymerization, such as ethyl eosin, eosin Y, fluorescein, 2,2-dimethoxy-2-phenyl acetophenone, 2-methoxy,2-phenylacetophenone, camphorquinone, rose bengal, methylene blue, erythrosin, phloxime, thionine, riboflavin, methylene green, acridine orange, xanthine dye, and thioxanthine dyes.

Cocatalysts useful with photoinitiating dyes are typically nitrogen based compounds capable of stimulating a free radical reaction. Primary, secondary, tertiary or quaternary amines are suitable cocatalysts, as are nitrogen atom containing electron-rich molecules. Cocatalysts include triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine and arginine. Examples of the dye/photoinitiator system include ethyl eosin with an amine, eosin Y with an amine, 2,2-dimethoxy-2-phenoxyacetophenone, 2-methoxy-2-phenoxyacetophenone, camphorquinone with an amine, and rose bengal with an amine.

In some cases, dye may absorb light and initiate polymerization, without any additional initiator such as the amine. In these cases, only the dye and a monomer need be present to initiate polymerization upon exposure to light. The generation of free radicals is terminated when the laser light is removed. Some photoinitiators, such as 2,2-dimethoxy-2-phenylacetophenone, do not require any auxiliary amine to induce photopolymerization; in these cases, the presence of dye, monomer and an appropriate wavelength light is sufficient for photopolymerization.

Preferred light sources include various lamps and lasers such as those which have a wavelength of about 320–800 nm. This light can be provided by any appropriate source able to generate the desired radiation, such as a mercury lamp, longwave UV lamp, He-Ne laser, an argon ion laser, etc. In a preferred embodiment, a UV source is used to polymerize a UV photopolymerizeable gel. Similarly, the light source used is typically selected based upon the chemistry which is to be affected by the source.

Similarly, a variety of gels can be selectively polymerized by exposure to heat. As described herein, selective heat control using applied current is easily performed in the microfluidic apparatus of the invention, providing for simplified control of gel polymerization through thermal processes. Examples include initiation by thermal initiators, which form free radicals at moderate temperatures, such as benzoyl peroxide, with or without triethanolamine, potassium persulfate, with or without tetramethylethylenediamine, and ammonium persulfate with sodium bisulfite.

For either the thermal or photopolymerization methods herein, monomer is pumped, e.g., in aqueous buffer, into a channel or channel region using electroosmotic flow, or using a pressure gradient. After selective exposure to light or heat, as appropriate, unpolymerized materials are removed, typically using electroosmotic flow, but optionally using a pressure gradient, from regions where monomer material is undesirable.

In another embodiment, the first fluid is polymerized by selectively exposing certain channel regions to an activator or cross-linker. For example, where the fluid is polyacrylamide, the activator/cross linker can be TEMED and APS. In this embodiment, the reagents are placed into a well and electrokinetically loaded into selected channel regions of a microfluidic substrate. After selective exposure to activator/cross linker as appropriate, unpolymerized materials are removed from regions where monomer material is undesirable, typically using electroosmotic flow (but optionally using a pressure gradient). Often the material will be shunted to one or more waste buffer where the material is optionally removed, e.g., by pipetting or electropipeting the material out of the well.

In another embodiment, a sieving matrix is deposited throughout a channel or channels of a microfluidic device in a form which is subject to electroosmosis (i.e., the matrix moves electrokinetically in the channel). The matrix is then selectively replaced by a second fluidic phase (e.g., a buffer) in selected regions of a channel by electrokinetically loading the buffer in the selected region.

In an additional embodiment, a first fluidic phase is loaded into multiple channels of a micrbfluidic device and polymerized in place. Selective components which solubilize the polymerized gel are then loaded (e.g., electrokinetically or under pressure) into channel regions where polymerized product is not desired. The selected components dissolve the polymerized gel. Example of solubilization compounds include acids, bases and other chemicals. In one preferred embodiment, at least two compounds are used to dissolve polymerized products, where both products need to be present to dissolve the polymer. This provides for fine control of dissolution, e.g., where each chemical is under separate electrokinetic control. An example of such a chemical pair is DTT(N,N'-bis(acrylol)cystamine or (1,2-dihydroxyethylene-bis-acrylamide) [DHEBA] and sodium periodiate or calcium alginate+EDTA or TCEP-HCL and N,N'-bis(acryloyl)cystamine. A variety of such materials are known.

Microfluidic Apparatus Applications—PCR and In Vitro Amplification

The multi-phasic apparatus of the invention are particularly useful for performing experimental or diagnostic procedures which combine fluid mixing and product separatory aspects. For example, in a first fluidic phase, reactions such as PCR are performed, followed by separation in a sieving matrix in different channel region. Bench scale in vitro amplification techniques suitable for amplifying sequences to provide a nucleic acid e.g., as a diagnostic indicator for the presence of the sequence, or for subsequent analysis, sequencing or subcloning are known.

In brief, the most common form of in vitro amplification, i.e., PCR amplification, generally involves the use of one strand of the target nucleic acid sequence as a template for producing a large number of complements to that sequence. As used herein, the phrase "target nucleic acid sequence" generally refers to a nucleic acid sequence, or portion of a nucleic acid sequence that is the subject of a particular fluidic operation, e.g., analysis, amplification, identification or the like. Generally, two primer sequences complementary to different ends of a segment of the complementary strands of the target sequence hybridize with their respective strands of the target sequence, and in the presence of polymerase enzymes and nucleoside triphosphates, the primers are extended along the target sequence through the action of the polymerase enzyme (in asymmetric PCR protocols, a single primer is used). The extensions are melted from the target sequence by raising the temperature of the reaction mixture, and the process is repeated, this time with the additional copies of the target sequence synthesized in the preceding steps. PCR amplification typically involves repeated cycles of denaturation, hybridization and extension reactions to produce sufficient amounts of the target nucleic acid, all of which are carried out at different temperatures. Typically, melting of the strands, or heat denaturation, involves temperatures ranging from about 90° C. to 100° C. for times ranging from seconds to minutes. The temperature is then cycled down, e.g., to between about 40° C. and 65° C. for annealing, and then cycled up to between about 70° C. and 85° C. for extension of the primers along the target strand.

Examples of techniques sufficient to direct persons of skill through in vitro amplification methods at benchtop scales, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al, (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

The use of PCR for amplifying nucleic acids is ubiquitous in molecular biology for the amplification and detection of nucleic acids. PCR technologies are well-suited to forensic analysis, paternity testing, maternity testing, infectious disease diagnosis (e.g., detection of a nucleic acid from a pathogenic organism such as a virus, e.g., HIV, HTLV, herpes virus, etc.), cancer diagnosis (e.g., for the detection of oncogenic gene products such as p53 nucleic acids, Her 2 nucleic acids, etc.). Use of PCR for these techniques is well known and adaptable to use with the present invention.

In one aspect, PCR or other thermal reaction reagents (e.g., LCR reagents) such as thermostable polymerase, DNA template, primers, nucleotides and buffers are mixed in a microchannel or chamber, with the entire microfluidic substrate (e.g., a LABCHIP™ from Caliper Technologies) being subject to repeated cycles of heating and cooling, e.g., on a thermocycler or by switching between a hot plate and a heat sink.

In a second more preferred embodiment, variations in channel thickness and/or voltage are used selectively to heat selected regions of a channel which contain a PCR reaction. PCR amplification is particularly well suited to this use in the apparatus, methods and systems of the invention. Thermocycling amplification methods, including PCR and LCR, are conveniently performed in microscale devices, making iterative fluidic operations involving PCR well suited to use in methods and devices of the present invention (see also, U.S. Pat. Nos. 5,498,392 and 5,587,128 to Willingham et al.). Accordingly, in one preferred embodiment, generation of amplicons such as sequencing templates using PCR, or direct sequencing of nucleic acids by PCR (e.g., using nuclease digestion as described supra) is performed with the integrated systems and devices of the invention.

Thermocycling in microscale devices, including thermocycling by joule heating is described in co-pending application USSN 60/056,058, entitled "ELECTRICAL CURRENT FOR CONTROLLING FLUID TEMPERATURE IN MICROCHANNELS" filed Sep. 2, 1997 by Calvin Chow, Anne R. Kopf-Sill and J. Wallace Parce; in U.S. Pat. No. 5,965,410; provisional patent application USSN 60/068,311, entitled "Closed Loop Biochemical Analyzer" by Knapp, filed Dec. 19, 1997 and in U.S. Pat. No. 6,235,471. In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through a first fluidic phase in a first channel region for heating purposes, as well as for material transport. In exemplary embodiments, the fluid of the first fluidic phase passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like.

In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance:

$$POWER = I^2 R$$

where

POWER=power dissipated in fluid;

I=electric current passing through fluid; and

R=electric resistance of fluid.

The above equation provides a relationship between power dissipated ("POWER") to current ("I") and resistance ("R"). In some of the embodiments, which are directed toward moving fluid in channels, e.g., to provide mixing, electrophoretic separation, or the like, a portion of the power goes into kinetic energy of moving the fluid through the channel. However, it is also possible to use a selected portion of the power to controllably heat fluid in a channel or selected channel regions. A channel region suitable for heating is often narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid to correspondingly increase fluid temperature.

To selectively control the temperature of fluid at a region of the channel, a power supply applies voltage and/or current in one of many ways. For instance, a power supply can apply direct current (i.e., DC) or alternating current (AC), which passes through the channel and into a channel region which is smaller in cross-section, thereby heating fluid in the region. This current is selectively adjusted in magnitude to complement any voltage or electric field that is applied to move fluid in and out of the region. AC current, voltage, and/or frequency can be adjusted, for example, to heat the fluid without substantially moving the fluid. Alternatively, a power supply can apply a pulse or impulse of current and/or voltage, which passes through the channel and into a channel region to heat fluid in the region. This pulse is selectively adjusted to complement any voltage or electric field that is applied to move fluid in and out of the region. Pulse width, shape, and/or intensity can be adjusted, for example, to heat the fluid substantially without moving the fluid or to heat the fluid while moving the fluid. Still further, the power supply can apply any combination of DC, AC, and pulse, depending upon the application. In practice, direct application of electric current to fluids in the microchannels of the invention results in extremely rapid and easily controlled changes in temperature.

A controller or computer such as a personal computer monitors the temperature of the fluid in the region of the channel where the fluid is heated. The controller or computer receives current and voltage information from, for example, the power supply and identifies or detects temperature of fluid in the region of the channel. Depending upon the desired temperature of fluid in the region, the controller or computer adjusts voltage and/or current to meet the desired fluid temperature. The controller or computer also can be set to be "current controlled" or "voltage controlled" or "power controlled" depending upon the application.

The region which is heated can be a "coil" which is optionally in a planar arrangement. Transfer of heat from the coil to a reaction channel through a substrate material is used to heat the reaction channel. Alternatively, the coil itself is optionally the reaction channel.

A voltage is applied between regions of the coil to direct current through the fluid for heating purposes. In particular, a power supply provides a voltage differential between regions of the coil. Current flows between the regions and traverses a plurality of coils or coil loops (which can be planar), which are defined by a substrate. Shape and size of the coils can influence an ability of current to heat the fluid in the coil. As current traverses through the fluid, energy is transferred to the fluid for heating purposes. Cooling coils can also be used. As a cooling coil, a fluid traverses from region to region in the coil, which can be placed to permit heat transfer through a substrate from a sample. The cooling fluid can be a variety of substances including liquids and gases. As merely an example, the cooling fluid includes aqueous solutions, liquid or gaseous nitrogen, and others. The cooling fluid can be moved between regions using any of the techniques described herein, and others. Further details are found in Chow et al., supra.

The introduction of electrical current into fluid causes heat (this procedure is referred to as "Joule heating"). In the examples of fluid movement herein where thermal effects are not desired, the heating effect is minimal because, at the small currents employed, heat is rapidly dissipated into the chip itself. By substantially increasing the current across the channel, rapid temperature changes are induced that can be monitored by conductivity. At the same time, the fluid can be kept static in the channel by using alternating instead of direct current. Because nanoliter volumes of fluid have tiny thermal mass, transitions between temperatures can be extremely short. Oscillations between any two temperatures above 0° C. and below 100° C. in 100 milliseconds have been performed.

Joule heating in microchannels is an example of how benchtop methods can be dramatically improved in the formats provided herein. PCR takes hours to perform currently, primarily because it takes a long time for conventional heating blocks to oscillate between temperatures. In addition, reagent cost is an obstacle to massive experimentation. Both these parameters are altered by orders of magnitude in the LabChip™ format.

In one aspect, PCR reaction conditions are controlled as a function of channel geometry. Microfabrication methods permit the manufacture of channels that have precise variations in cross sectional area. Since the channel resistance is inversely proportional to the cross sectional area, the temperature varies with the width and depth of the channel for a given flow of current. As fluid moves through a structure of varying cross sectional area, its temperature will change, depending on the dimensions of the channel at any given point. The amount of time it experiences a given temperature will be determined by the velocity of the fluid flow, and the length of channel with those dimensions. This concept is illustrated in FIG. 2. Nucleic acids of typical lengths have a low diffusion coefficient (about $10^{-7}$ cm/sec$^2$). Thus over the time frame necessary to affect amplification, DNA will only diffuse a few hundred microns. In a given channel, reactions of a few nanoliters will occupy a few millimeters. Thus in devices of convenient length (a few centimeters), many PCR reactions can be performed concurrently yielding new amplification products every few seconds per channel. In parallel formats, hundreds of separate reactions can be performed simultaneously. Because of its simplicity, throughput and convenience, this amplification unit is a preferred feature of many assays herein.

In FIG. 2, amplification reactions are performed concurrently in series using biased alternating current to heat the fluid inside the channel and move material through it. The time for each step of the reaction is controlled by determining the speed of movement and the length of channel having particular widths. Flow can be reversed to allow a single small channel region to be used for many separate amplifications.

As depicted, several samples are run simultaneously in channel 210. Sample 215 is in narrow channel region 220; in operation, this region is heated to, e.g., 95° C. (hot enough to denature nucleic acids present in sample 215, but cool enough that thermostable reagents such as Taq DNA polymerase are relatively stable due to the relative size of region 220 and the applied current. Concurrently, wide channel region 230 is heated, e.g., to 60° C. (cool enough for binding of primers in sample 225 and initiation of polymerase extension), due to the relative size of region 230 and the applied current. Concurrently, intermediate channel region 235 is heated, e.g., to 72° C. (hot enough to prevent unwanted non-specific primer-target nucleic acid interactions in sample 240 and cool enough to permit continued polymerase extension), due to the relative size of region 235 and the applied current. This process can be concurrently carried out with a plurality of additional channel regions such as narrow region 245, wide region 250 and intermediate region 255, with samples 260, 265 and 270.

Where possible, direct detection of amplified products can be employed. For example, differentially labeled competitive probe hybridization is used for single nucleotide discrimination. Alternatively, molecular beacons or single nucleotide polymerase extension can be employed. Homogeneous detection by fluorescence polarization spectroscopy can also be utilized (fluorescence polarization has been used to distinguish between labeled small molecules free in solution or bound to protein receptors).

PCR Chips

One aspect of the present invention is the surprising discovery that PCR can be performed in the presence of sieving matrix, and that the products of the PCR reaction are separable in the matrix in a microfludic channel (see also, the examples below).

Accordingly, in one aspect, the invention provides new method of performing PCR. In the methods, components of a PCR reaction mixture (i.e., the molecules which participate in a PCR reaction, such as PCR extension primers, nucleotide triphosphates, thermostable enzymes, ions and buffer components such as $Mg^{++}$, template DNAs, etc.) are mixed with a sieving matrix to provide a PCR sieving matrix mixture. The resulting mixture is then repetitively thermocycled as described supra to produce one or more PCR products.

In preferred embodiments, the components of the PCR reaction mixture are mixed with the sieving matrix in a microfluidic channel, e.g., a channel on a LABCHIP™. The apparatus can include one or more additional channels crossing the microfluidic channel and optionally includes fluid (or joule heating) means such as an electrokinetic controller. Detection regions in the channels, and corresponding detectors are also useful. The PCR products are typically electrophoresed through the channels to achieve product separation.

It will be appreciated that separations chips comprising a single matrix separations phase are produced as described above, thus, for this embodiment, multiple fluidic phases in the appratus are not necessary. However, additional fluidic phases can be placed in additional channels or channel regions in fluid communication with a channel region comprising the PCR sieving mixture for electrophoretic or electroosmotic movement of the PCR components or products in the chips. For example, in some aspects a PCR reaction product is selected for further manipulations such as cloning, sequencing or the like, all of which are performed in PCR chips (see also, USSN 60/068,311, entitled "Closed Loop Biochemical Analyzer" by Knapp, filed Dec. 19, 1997 and U.S. Pat. No. 6,235,471.

Microfluidic Apparatus Applications—DNA Sequencing

The multiphasic devices and methods of the present invention are also particularly applicable to nucleic acid sequencing. It will be appreciated that DNA sequencing reactions can be run in a first fluid phase of the apparatus, with separatory steps being performed in a sieving matrix.

The integrated systems of the invention are useful for sequencing a wide variety of nucleic acid constructs. Essentially any DNA template can be sequenced, with the selection of the nucleic acid to be sequenced depending upon the construct in hand by the sequencer. Thus, an initial step in the methods of the invention is the selection or production of a template nucleic acid to be sequenced.

Many methods of making recombinant ribo and deoxyribo nucleic acids, including recombinant plasmids, recombinant lambda phage, cosmids, yeast artificial chromosomes (YACs), P1 artificial chromosomes, Bacterial Artificial Chromosomes (BACs), and the like are known. The sequencing of large nucleic acid templates is advantageously performed by the present methods, systems and apparatus, because an entire nucleic acid can be sequenced by primer walking along the length of the template in several rapid cycles of sequencing.

Examples of appropriate cloning techniques for making nucleic acids, and instructions sufficient to direct persons of skill through most standard cloning and other template preparation exercises are found in Berger and Kimmel, *Guide to Molecular Cloning Techniques, Methods in Enymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al, eds., Current Protocols, a joint venture between Greene Publishing Associates, Inc. and John Wiley & Sons, Inc., (1997, supplement 37) (Ausubel). Basic procedures for cloning and other aspects of molecular biology and underlying theoretical considerations are also found in Lewin (1995) *Genes V* Oxford University Press Inc., NY (Lewin); and Watson et al. (1992) *Recombinant DNA Second Edition* Scientific American Books, NY. Product information from manufacturers of biological reagents and experimental equipment also provide information useful in known biological methods. Such manufacturers include the Sigma Chemical Company (Saint Louis, Mo.); New England Biolabs (Beverly, Mass.); R&D systems (Minneapolis, Minn.); Pharmacia LKB Biotechnology (Piscataway, N.J.); CLONTECH Laboratories, Inc. (Palo Alto, Calif.); Chem-Genes Corp., (Waltham Mass.) Aldrich Chemical Company (Milwaukee, Wis.); Glen Research, Inc. (Sterling, Va.); GIBCO BRL Life Technologies, Inc. (Gaithersberg, Md.); Fluka Chemica-Biochemika Analytika (Fluka Chemie AG, Buchs, Switzerland); Invitrogen (San Diego, Calif.); Perkin Elmer (Foster City, Calif.); and Strategene; as well as many other commercial sources known to one of skill.

In one aspect, the generation of large nucleic acids is useful in practicing the invention. It will be appreciated that such templates are particularly useful in some aspects where the methods and devices of the invention are used to sequence large regions of DNA, e.g., for genomics types of applications. An introduction to large clones such as YACs, BACs, PACs and MACs as artificial chromosomes is provided by Monaco and Larin (1994) *Trends Biotechnol* 12 (7): 280–286.

The construction of nucleic acid libraries of template nucleic acids is described in the above references. YACs and YAC libraries are further described in Burke et al. (1987) *Science* 236:806–812. Gridded libraries of YACs are described in Anand et al. (1989) *Nucleic Acids Res.* 17, 3425–3433, and Anand et al. (1990) *Nucleic Acids Res.* Riley (1990) 18:1951–1956 *Nucleic Acids Res.* 18(10): 2887–2890 and the references therein describe cloning of YACs and the use of vectorettes in conjunction with YACs. See also, Ausubel, chapter 13. Cosmid cloning is also well known. See, e.g., Ausubel, chapter 1.10.11 (supplement 13) and the references therein. See also, Ish-Horowitz and Burke (1981) *Nucleic Acids Res.* 9:2989–2998; Murray (1983) Phage Lambda and Molecular Cloning in *Lambda II* (Hendrix et al., eds) 395–432 Cold Spring Harbor Laboratory, NY; Frischauf et al. (1983) *J.Mol. Biol.* 170:827–842; and, Dunn and Blattner (1987) *Nucleic Acids Res.* 15:2677–2698, and the references cited therein. Construction of BAC and P1 libraries is well known; see, e.g., Ashworth et al. (1995) *Anal Biochem* 224 (2): 564–571; Wang et al. (1994) *Genomics* 24(3): 527–534; Kim et al. (1994) *Genomics* 22(2): 336–9; Rouquier et al. (1994) *Anal Biochem* 217(2): 205–9; Shizuya et al. (1992) *Proc Natl Acad Sci USA* 89(18): 8794–7; Kim et al. (1994) *Genomics* 22 (2): 336–9; Woo et al. (1994) *Nucleic Acids Res* 22(23): 4922–31; Wang et al (1995) *Plant* (3): 525–33; Cai (1995) *Genomics* 29 (2): 413–25; Schmitt et al. (1996) *Genomics* 1996 33(1): 9–20; Kim et al. (1996) *Genomics* 34(2): 213–8; Kim et al. (1996) *Proc Natl Acad Sci USA* (13): 6297–301; Pusch et al. (1996) *Gene* 183(1–2): 29–33; and, Wang et al. (1996) *Genome Res* 6(7): 612–9. In general, where the desired goal of a sequencing project is the sequencing of a genome or expression profile of an organism, a library of the organism's cDNA or genomic DNA is made according to standard procedures described, e.g., in the references above. Individual clones are isolated and sequenced, and overlapping sequence information is ordered to provide the sequence of the organism. See also, Tomb et al. (1997) *Nature* 539–547 describing the whole genome random sequencing and assembly of the complete genomic sequence of *Helicobacter pylori;* Fleischmann et al. (1995) *Science* 269:496–512 describing whole genome random sequencing and assembly of the complete *Haemophilus influenzae* genome; Fraser et al. (1995) *Science* 270:397–403 describing whole genome random sequencing and assembly of the complete *Mycoplasma genitalium* genome and Bult et al. (1996) *Science* 273:1058–1073 describing whole genome random sequencing and assembly of the complete *Methanococcus jannaschii* genome.

The nucleic acids sequenced by this invention, whether RNA, cDNA, genomic DNA, or a hybrid of the various combinations, are isolated from biological sources or synthesized in vitro. The nucleic acids of the invention are present in transformed or transfected whole cells, in transformed or transfected cell lysates, or in a partially purified or substantially pure form.

In order to take advantage of the very small quantities of reagents required by the chip, and to make a system scalable to millions of experiments, a solid phase reagent interface uniquely suited to high throughput LabChip processing is desirable. Several interfaces that make use of reagents dried in microarrays on a solid surface are described in USSN 60/068,311, entitled "Closed Loop Biochemical Analyzer" by Knapp, filed Dec. 19, 1997 and U.S. Pat. No. 6,235,471. These configurations are suited to the needs of diagnostic products in which elements need to be standardized, convenient, and have acceptable shelf-life.

In brief, oligonucleotide primers are chosen from a pool of possible sequencing primers upon determination of an initial portion of the DNA sequence. With iterative utilization of this strategy, it is possible to primer walk through an entire sequence without synthesizing new primers. A template nucleic acid is selected and introduced into a reaction channel in a microfluidic (generally electroosmotic) device of the invention. The template is optionally amplified, e.g., by introducing PCR or LCR reagents into the channel and performing cycles of heating and cooling on the template. Alternatively, e.g., where the source of template is from an abundant sequence such as a cloned nucleic acid, further amplification can be unnecessary. In addition to amplification procedures, a PCR nuclease chain termination procedure can also be used for direct sequencing in the methods of the invention. Porter et al. (1997) *Nucleic Acids Research* 25(8):1611–1617 describe the biochemistry of PCR chain termination methods.

Sequencing reagents are added to the template nucleic acid and a sequencing reaction is performed appropriate to the particular reaction in use. Many appropriate reactions are known, with the Sanger dideoxy chain termination method being the most common. See, Sanger et al. (1977) *Proc. Nat. Acad. Sci., USA* 74:5463–5467. The primer used to prime synthesis is typically selected from a pre-synthesized set of nucleic acid primers, preferably a set including many or all of the primers for a particular primer length. In a preferred aspect, modular primers are used. For modular primer strategies, see, Beskin et al. (1995) *Nucleic Acids Research* 23(15):2881–2885). A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al. (1997) *Nucleic Acids Research* 25(4):800–805.

After the sequencing reaction is run, the products are separated by size and/or charge in an analysis region of the microfluidic device which comprises a second fluidic phase adapted for separation of nucleic acids, such as a sieving matrix as discussed above. As discussed herein, the devices of the invention can be used to electrophoretically separate macromolecules by size and/or charge. The separated products are detected, often as they pass a detector (nucleic acids are typically labeled with radioactive nucleotides or fluorophores; accordingly appropriate detectors include spectrophotometers, fluorescent detectors, microscopes (e.g., for fluorescent microscopy) and scintillation counting devices). Detection of size separated products is used to compile sequence information for the region being sequenced. A computer is typically used to select a second primer from the pre-synthesized primer set which hybridizes to the sequenced region, and the process is iteratively repeated with the second primer, leading to sequencing of a second region, selection of a third primer hybridizing to the second region, etc.

Selecting and Making Primers for Sequencing and PCR

Oligonucleotides for use as primers or probes, e.g., in sequencing or PCR or non-thermal amplification reactions in microfluidic apparatus are typically synthesized chemically according to the solid phase phosphoramidite triester method described by Beaucage and Caruthers (1981), *Tetrahedron Letts.,* 22(20):1859–1862, e.g., using an automated synthesizer, as described in Needham-VanDevanter et al. (1984) *Nucleic Acids Res.,* 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

While primers can hybridize to any of a number of sequences, selecting optimal primers is typically done using computer assisted consideration of available sequences and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length, G:C ratio, uniqueness in the given sequence, etc.) based upon the known sequence. The selection of the hybridization properties of the primer is dependent on the desired hybridization and discrimination properties of the primer. In general, the longer the primer, the higher the melting temperature. In addition, it is more difficult to generate a set of primers which includes all possible oligonucleotides for a given length, as the required number of primers increases exponentially. For example, all possible 3-mers requires $4^3$ primers, all possible 4-mers requires $4^4$ primers, all possible 5-mers requires $4^5$ primers, all possible 6-mers requires $4^6$ primers, etc. Standard sequencing primers are often in the range of 15–20 nucleotides in length, which would require sets of $4^{15}$ to $4^{20}$ nucleotides, or $1.1 \times 10^9$ to $1.1 \times 10^{12}$ primers.

While it is possible to make such large sets of primers using combinatorial chemical techniques, the associated problems of storing and retrieving billions or even trillions of primers make these primer sets less desirable. Instead, smaller sets of primers used in a modular fashion are desirable.

For example, Ulanovsky and co-workers have described the mechanism of the modular primer effect (Beskin et al. (1995) *Nucleic Acids Research* 23(15):2881–2885) in which short primers of 5–6 nucleotides can specifically prime a template-dependent polymerase enzyme when 2–3 contiguously annealing, but unligated, primers are used in a polymerase dependent reaction such as a sequencing reaction. Polymerase enzymes are preferentially engaged by longer primers, whether modular or conventional, accounting for the increased specificity of modular primers. Because it is possible to synthesize easily all possible primers with 5–6 nucleotides (i.e., $4^5$ to $4^6$ or 1024 to 4096 primers), it is possible to generate and utilize a universal set of nucleotide primers, thereby eliminating the need to synthesize particular primers to extend nucleotide sequencing reactions of nucleotide templates. In an alternative embodiment, a ligase enzyme is used to ligate primers which hybridize to adjacent portions of a template, thereby providing a longer primer.

A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al. (1997) *Nucleic Acids Research* 25(4):800–805. Thus, whether standard Sanger-style sequencing or direct PCR sequencing using boronated nucleotides and a nuclease (see, Porter et al. 1997, supra.) are desired, small sets of short primers are sufficient for use in sequencing and PCR and are desirable.

It is expected that one of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology*, volume 20; and Tijssen (1993) *Laboratory Techniques in biochemistry and molecular biology—hybridization with nucleic acid probes*, e.g., part I chapter 2 "overview of principles of hybridization and the strategy of nucleic acid probe assays", Elsevier, N.Y. provide a basic guide to nucleic acid hybridization. Innis supra provides an overview of primer selection.

One of skill will recognize that the 3' end of an amplification primer is more important for PCR than the 5" end. Investigators have reported PCR products where only a few nucleotides at the 3" end of an amplification primer were complementary to a DNA to be amplified. In this regard, nucleotides at the 5' end of a primer can incorporate structural features unrelated to the target nucleic acid; for instance, in one embodiment, a sequencing primer hybridization site (or a complement to such as primer, depending on the application) is incorporated into the amplification primer, where the sequencing primer is derived from a primer used in a standard sequencing kit, such as one using a biotinylated or dye-labeled universal M13 or SP6 primer. These structural features are referred to as constant primer regions. The primers are typically selected so that there is no complementarity between any known target sequence and any constant primer region. One of skill will appreciate that constant regions in primer sequences are optional.

The primers are selected so that no secondary structure forms within the primer. Self-complementary primers have poor hybridization properties, because the complementary portions of the primers self hybridize (i.e., form hairpin structures). Modular primers are selected to have minimal cross-hybridization, thereby preventing competition between individual primers and a template nucleic acid and preventing duplex formation of the primers in solution, and possible concatenation of the primers during PCR. If there is more than one constant region in the primer, the constant regions of the primer are selected so that they do not self-hybridize or form hairpin structures.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector™ program from Kodak. An alternate program is the MFOLD program (Genetics Computer Group, Madison Wis.) which predicts secondary structure of, e.g., single-stranded nucleic acids. In addition to programs for primer selection, one of skill can easily design simple programs for any or all of the preferred selection steps.

Integrated Multiphasic Microfluidic Apparatus and Systems

Multiphasic analysis systems are provided, for example for performing nucleic acids-based diagnostic and sequencing applications, e.g., in a reference laboratory setting. The system typically has several components: a multi-phasic microfluidic specimen and reagent handling system; an "operating system" for processing integrated microfluidic experimentation steps; application-specific analysis devices (optionally referred in this application e.g., as "LabChips™" (LabChip™ is a trademark of Caliper Technologies, Corp., Palo Alto Calif.); a label detection system, and multiple software components that allow the user to interact with the system, and run processing steps, interpret data, and report results.

The microfluidic apparatus of the invention typically comprise a substrate in which fluidic reagents, mixtures of reagents, reactants, products or the like are mixed and analyzed, in channels comprising different fluidic phases. A wide variety of suitable substrates for use in the devices of the invention are described in U.S. Ser. No. 08/761,575, entitled "High Throughput Screening Assay Systems in Microscale Fluidic Devices" by Parce et al. A microfluidic substrate holder is optionally incorporated into the devices of the invention for holding and/or moving the substrate during an assay. The substrate holder optionally includes a substrate viewing region for analysis of reactions carried out on the substrate. A label detector mounted proximal to the substrate viewing region to detect formation of products and/or passage of reactants along a portion of the substrate is provided. A computer, operably linked to the analyte detector, monitors formation of reactants, separation of sequencing products, or the like. An electrokinetic component typically provides for movement of the fluids on the multiphasic substrate.

A principal component of nucleic acid analysis is molecular partition, performed, e.g., in a separatory phase of the present invention. In addition, the dexterous fluidics in the microfluidic devices herein produce exquisite control over injection volume—a parameter determining resolution in molecular partitioning (typically, in the multi-phasic apparatus of the invention, stacking of components at the interface between fluidic phases provides for enhanced resolution). Aside from biochemistry and analytical capabilities in microdevices, systems that automate access to reagents and specimens are highly useful for the integrated multiphasic systems herein. In high throughput pharmaceutical screening a "World-to-chip" interface capable of importing samples from conventional liquid vessels (such as test tubes or 384-well plates), or from solid dots of reagent on substrates is useful.

Accordingly, in one embodiment, a "sipping" strategy for introducing solubilized reagents or samples into a microfluidic substrate from a standard microplate is used. This is adapted to elements of nucleic acids testing, for example to allow for random access to a library of probes or primers.

In a preferred aspect, the invention provides a multi-phasic "closed-loop" device for determining the entire sequence of an unknown DNA molecule of interest by iteratively sequencing sub regions of the molecule of interest and compiling the subsequence information. Closed loop sequencing strategies are described in provisional patent application USSN 60/068,311, entitled "Closed Loop Biochemical Analyzer" by Knapp, filed Dec. 19, 1997 and U.S. Pat. No. 6,235,471.

In brief, many robotic systems are now available that can deposit arrays of individual solutions at high densities (1000 per square centimeter and greater). These are typically used as capture elements in heterogeneous phase biochemical assays such as nucleic acids hybridization. The same approach can be used to deposit elements of solution phase reactions (PCR primers, probes, sequencing primers, etc.). Using these approaches, systems that access solid phase reagents at densities of up to 1000 spots per square centimeter are made.

As described above, a preferred integrated method of the invention incorporates the use of pre-synthesized sets of primers for sequencing and/or PCR, and or reagents to be tested in drug screening assays. A device of the invention preferably includes a primer storage and/or primer transport mechanism for delivering selected primers to a reaction channel in the microfluidic device. Exemplary storage mechanisms optionally include components adapted to holding primers in a liquid or lyophilized form, including containers, containers with separate compartments, plates with wells (e.g., small microtiter plates with hundreds or thousands of wells) membranes, matrices, arrays of polymers, or the like. Additional embodiments for handling dried reagents on solid substrates are shown below.

In one embodiment, the primer storage area is physically separated from the substrate. In this embodiment, the primers can be loaded onto the substrate, either manually, or using an automated system. For example, a Zymate XP (Zymark Corporation; Hopkinton, Mass.) automated robot using a Microlab 2200 (Hamilton; Reno, Nev.) pipetting station can be used to transfer parallel samples to regularly spaced wells in a manner similar to transfer of samples to microtiter plates. If the primers are stored in lyophilized form (e.g., dried on a substrate), a portion of the lyophilized primer is typically suspended in an aqueous solution to facilitate transfer to a microfluidic substrate. An electropipettor can be used to select and transport samples to a microfluidic substrate from a well plate, or from any region of a microfluidic substrate. Because integration of the electropipettor with the microfluidic substrates of the invention is relatively simple, electropipettor embodiments are preferred.

In preferred embodiments including an electropipettor, a variety of storage systems for storing reagents, such as primers for delivery to the microfluidic devices of the invention, are applicable. Compounds are conveniently sampled with the electropipettor from well plates or from immobilized samples stored on a matrix (e.g., a porous, hydrophilic, or hydrophobic matrix, or from driedsamples stored on a substrate such as nitrocellullose, nylon or nytran membrane. In embodiments where the samples are dried, the samples are solubilized using the electropipettor, which can be operated to expel a small volume of fluid onto the dried reagent, followed by pipetting the expelled fluid comprising the reagent into the electropipettor. See also, U.S. Pat. No. 5,779,868.

Generally, samples are optionally applied to the sample matrix by any of a number of well known methods. For example, sample libraries are spotted on sheets of a sample matrix using robotic pipetting systems which allow for spotting of large numbers of compounds. Alternatively, the sample matrix is treated to provide predefined areas for sample localization, e.g., indented wells, or hydrophilic regions surrounded by hydrophobic barriers, or hydrophobic regions surrounded by hydrophilic barriers (e.g., where samples are originally in a hydrophobic solution), where spotted materials will be retained during the drying process. Such treatments then allow the use of more advanced sample application methods, such as those described in U.S. Pat. No. 5,474,796, wherein a piezoelectric pump and nozzle system is used to direct liquid samples to a surface. Generally, however, the methods described in the '796 patent are concerned with the application of liquid samples on a surface for subsequent reaction with additional liquid samples. However, these methods are readily modified to provide dry spotted samples on a substrate. Similarly, the use of ink-jet printing technology to print biological and chemical reagents onto substrates is well developed. See, e.g., Wallace (1996) *Laboratory Automation News* 1(5):6–9 where ink-jet based fluid microdispensing for biochemical applications is described.

Similarly, cleavable linkers attaching compounds to an array can be used to store the compounds in an array, followed by cleavage from the array. A variety of cleavable linkers, including acid cleavable linkers, light or "photo" cleavable linkers and the like are known in the art. Exemplar arrays are described in Pirrung et al., U.S. Pat. No. 5,143,854 (see also, PCT Application No. WO 90/15070), Fodor et al., PCT Publication No. WO 92/10092 Fodor et al. (1991) *Science*, 251: 767–777; Sheldon et al. (1993) Clinical Chemistry 39(4): 718–719; Kozal et al (1996) *Nature Medicine* 2(7): 753–759 and Hubbell U.S. Pat. No. 5,571,639. Immobilization of assay components in an array is typically be via a cleavable linker group, e.g., a photolabile, acid or base labile linker group. Accordingly, the assay component is typically released from the assay e.g., by exposure to a releasing agent such as light, acid, base or the like prior to flowing the test compound down the reaction channel. Typically, linking groups are used to attach polymers or other assay components during the synthesis of the arrays. Thus, preferred linkers operate well under organic and/or aqueous conditions, but cleave readily under specific cleavage conditions. The linker is optionally provided with a spacer having active cleavable sites. In the particular case of oligonucleotides, for example, the spacer is selected from a variety of molecules which can be used in organic environments associated with synthesis as well as aqueous environments, e.g., associated with nucleic acid binding studies. Examples of suitable spacers are polyethyleneglycols, dicarboxylic acids, polyamines and alkylenes, substituted with, for example, methoxy and ethoxy groups. Linking groups which facilitate polymer synthesis on solid supports and which provide other advantageous properties for biological assays are known. In some embodiments, the linker provides for a cleavable function by way of, for example, exposure to an acid or base. Additionally, the linkers optionally have an active site on one end opposite the attachment of the linker to a solid substrate in the array. The active sites are optionally protected during polymer synthesis using protecting groups. Among a wide variety of protecting groups which are useful are nitroveratryl (NVOC) α-methylnitroveratryl (Menvoc), allyloxycarbonyl (ALLOC), fluorenylmethoxycarbonyl (FMOC), α-methylnitro-piperonyloxycarbonyl (MeNPOC), —NH—FMOC groups, t-butyl esters, t-butyl ethers, and the like. Various exemplary protecting groups are described in, for example, Atherton et al., (1989) *Solid Phase Peptide Synthesis,* IRL Press, and Greene, et al. (1991) *Protective Groups In Organic Chemistry,* 2nd Ed., John Wiley & Sons, New York, N.Y.

Other immobilization or spotting methods are similarly employed. For example, where samples are stable in liquid form, sample matrices can include a porous layer, gel or other polymer material which retain a liquid sample without allowing excess diffusion, evaporation or the like, but permit withdrawal of at least a portion of the sample material, as desired. In order to draw a sample into an electropipettor, the pipettor will free a portion of the sample from the matrix, e.g., by dissolving the matrix, ion exchange, dilution of the sample, and the like.

Whether the storage substrate is a filter, membrane, microtiter plate or other material holding reagents of interest, the substrate can conveniently be moved using a mechanical armature. Typically, the spatial location (or "physical address") of the reagents on the substrate are known. The armature moves the substrate relative to the microfluidic substrate (and electropipettor, where applicable) so that the component for transferring reagent from the substrate to the channels and wells of a microfluidic substrate (e.g., an electropipettor) contacts the desired reagent. Alternatively, the microfluidic substrate or electropipettor can be moved by an armature relative to the storage substrate to achieve the same effect. Similarly, both the storage substrate and the microfluidic substrate can be moved by the mechanical armature to achieve the same effect. In another aspect, the microfluidic substrate, storage substrate or transferring component (e.g., electropipettor) can be manually manipulated by the operator.

A variety of electropipettors, including "resolubilization" pipettors for solubilizing dried reagents for introduction into microfluidic apparatus are described in U.S. Pat. No. 5,779,868, supra. In brief, an electropipettor pipettor having separate channels is fluidly connected to an assay portion of the microfluidic device (i.e., a microfluidic substrate having the reaction and/or analysis and/or separation channels, wells or the like). In one typical embodiment, the electropipettor has a tip fluidly connected to a channel under electroosmotic control. The tip optionally includes features to assist in sample transfer, such as a recessed region to aid in dissolving samples. Fluid can be forced into our out of the channel, and thus the tip, depending on the application of current to the channel. Generally, electropipettors utilize electrokinetic or "electroosmotic" material transport as described herein, to alternately sample a number of test compounds, or "subject materials," and spacer compounds. The pipettor then typically delivers individual, physically isolated sample or test compound volumes in subject material regions, in series, into the sample channel for subsequent manipulation within the device. Individual samples are typically separated by a spacer region of low ionic strength spacer fluid. These low ionic strength spacer regions have higher voltage drop over their length than do the higher ionic strength subject material or test compound regions, thereby driving the electrokinetic pumping, and preventing electrophoretic bias. On either side of the test compound or subject material region, which is typically in higher ionic solution, are fluid regions referred to as first spacer regions (also referred to as high salt regions or "guard bands"), that contact the interface of the subject material regions. These first spacer regions typically comprise a high ionic strength solutions to prevent migration of the sample elements into the lower ionic strength fluid regions, or second spacer regions, which would result in electrophoretic bias. The use of such first and second spacer regions in described in greater detail in U.S. Pat. No. 5,779,868, supra. Spacers are not, however, required, particularly in the embodiments where transported components such as primers have the same charge and mass. It will be appreciated that embodiments using identically (or nearly identically) sized primers, such as modular primers, can be used without guard bands.

In an additional aspect, the present invention provides kits embodying the methods and apparatus herein. Kits of the invention optionally comprise one or more of the following: (1) an apparatus or apparatus component as described herein; (2) instructions for practicing the methods described herein, and/or for operating the apparatus or apparatus components herein; (3) one or more assay component; (4) a container for holding apparatus or assay components, and, (5) packaging materials.

In a further aspect, the present invention provides for the use of any apparatus, apparatus component or kit herein, for the practice of any method or assay herein, and/or for the use of any apparatus or kit to practice any assay or method herein.

EXAMPLES

The following examples are provided by way of illustration only and not by way of limitation. Those of skill will readily recognize a variety of noncritical parameters, which are changed or modified to yield essentially similar results.

Example 1
Integrated Analysis on Multi-phasic Microfluidic Apparatus

This example describes three experiments in which multiple operations in a biochemical assay were run on a chip. It demonstrates the ability to integrate functions such as complex (blood) sample preparation, specialized reactions (polymerase chain reaction, PCR), and sophisticated analysis (DNA size separation) in a single format on a multiphasic microfluidic apparatus.

In the first experiment we used a Caliper LabChip™ to load DNA template, run the PCR reaction, and then size the resulting PCR product by gel separation. In the second experiment we used whole blood as the source of DNA. The third experiment also starts with whole blood with an alternate method of sample preparation.

Figure 3A:
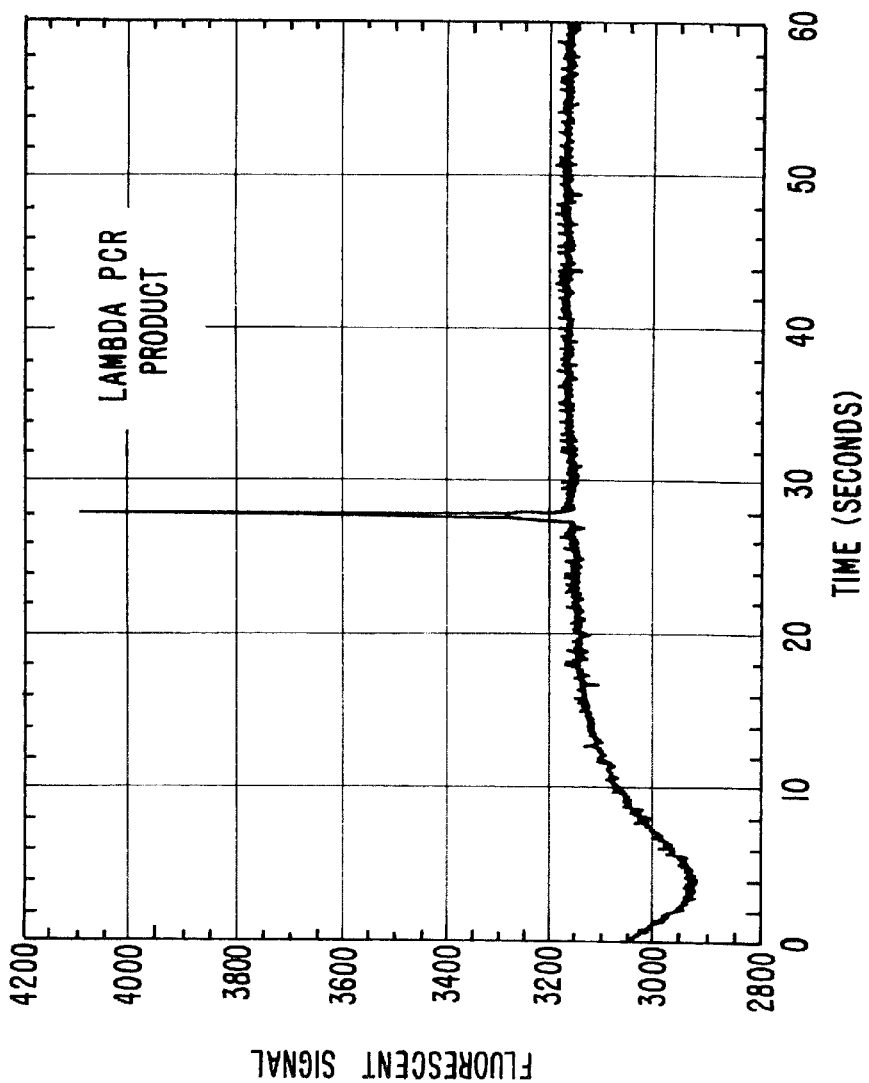
FIG. 3A a graph of PCR product separation.

All three experiments were done on a "12A" chip which is shown on the right-hand-side of FIG. 3. The entire chip was first filled with a sieving matrix gel. The cross-channel fluid was replaced with PCR mix suitable to amplify an approximately 500 bp segment of the bacteriophage Lambda. The loaded chip was placed on a thermocycler (MJ Research) and the temperature cycled to amplify the DNA in the wells and the channel. At the end of the cycling procedure, the chip was placed on a microscope detection station and the product was electrokinetically injected into the sieving channel. The peak which is shown in the accompanying electropherogram on FIG. 3 at 27–28 seconds corresponds to the Lambda 500-bp product.

Figures 4A, 4B:
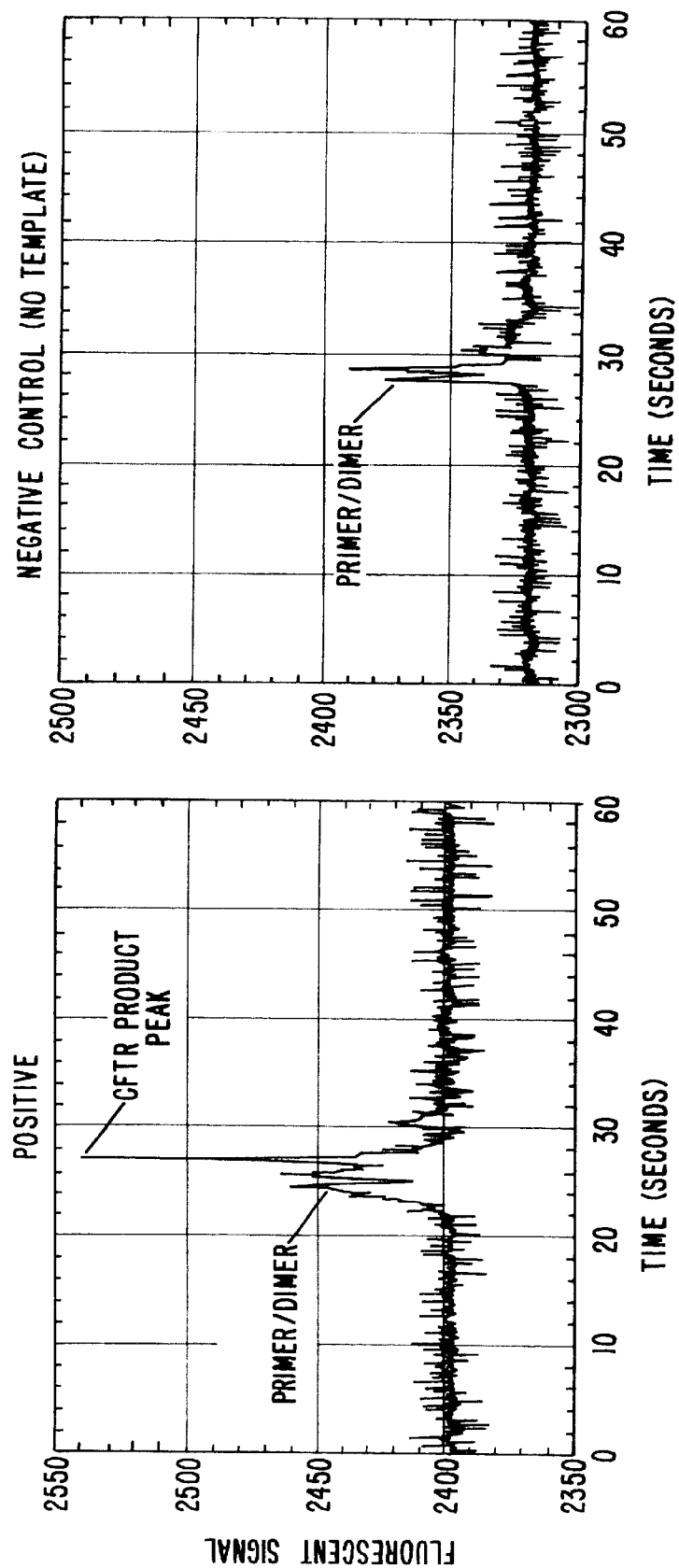
FIGS. 4A–4B shows two graphs of data from PCR of CFTR from whole blood.

In the second experiment whole blood mixed with PCR reaction mix (1% blood) was placed in the wells of the same type of chip. The chip was placed on a thermal cycler and cycled with a few additional steps at the beginning to aid in the amplification of blood. The amplified product was separated in the gel-filled channel and the product of the reaction is shown in FIG. 4. A negative control in which no blood was added to the mix was run with the same procedure and no peak is seen in that run. The electropherograms showing the positive an negative runs are shown in FIG. 4.

Figure 5:
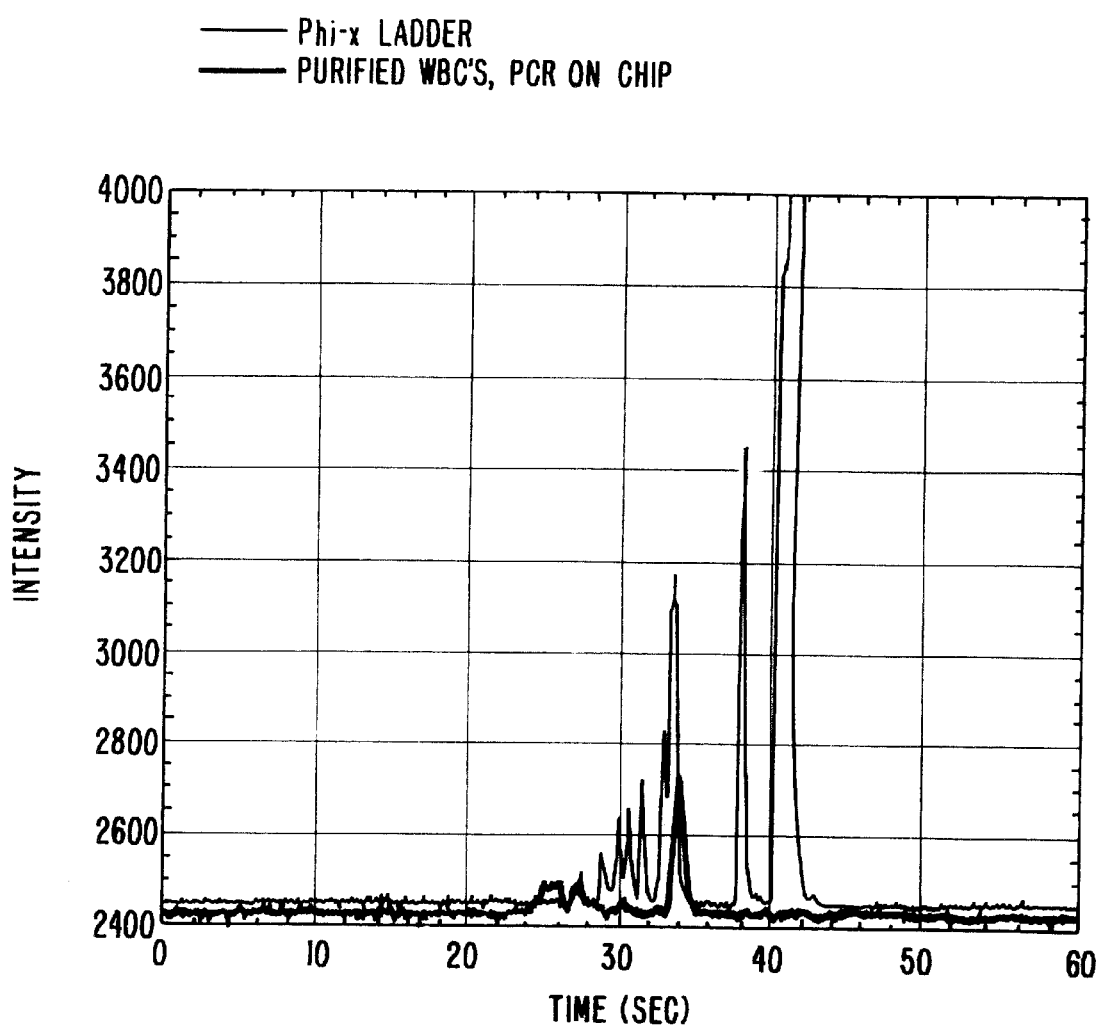
FIG. 5 is a graph of data from PCR amplification of purified WBCs.
Figure 6:
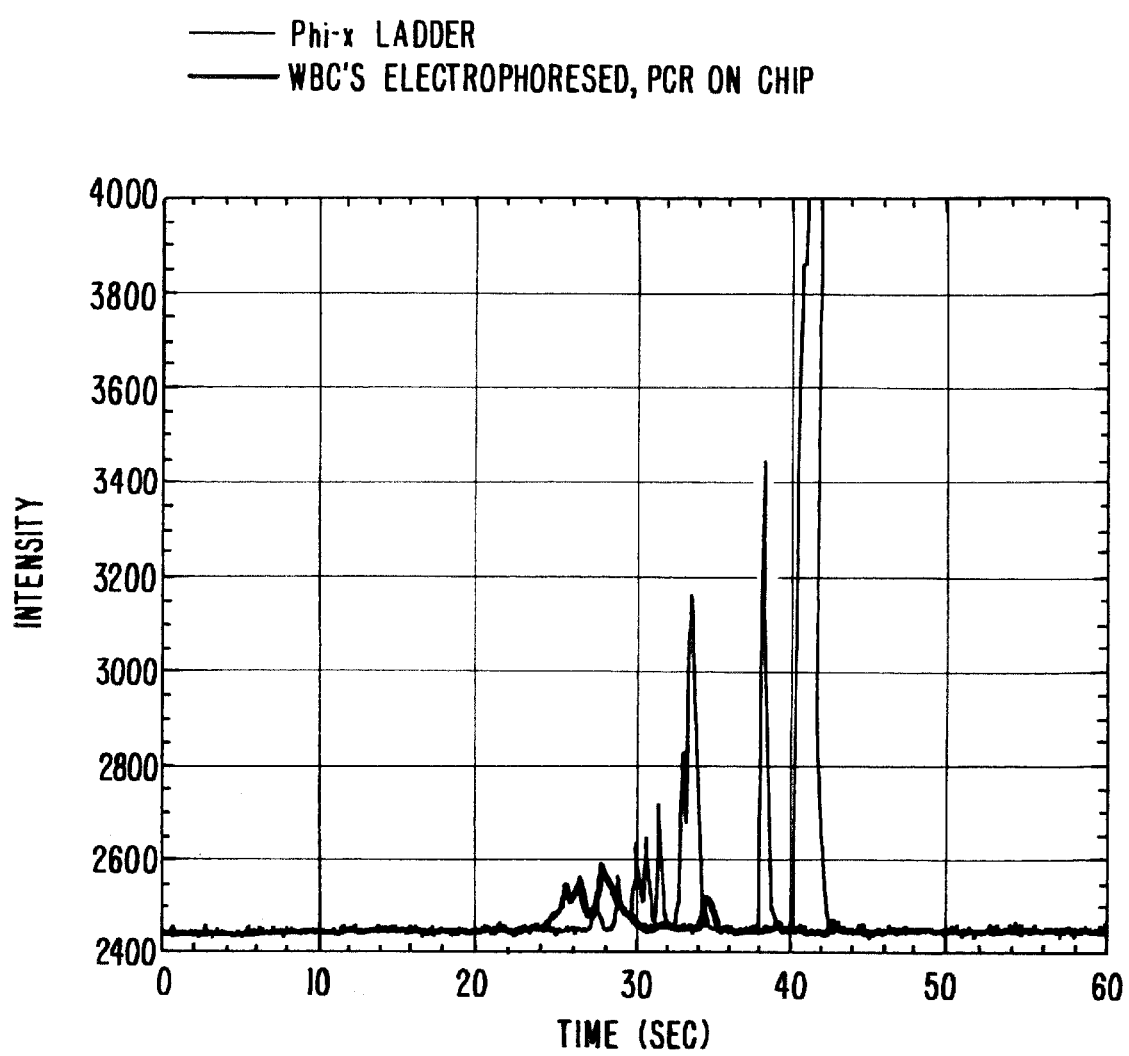
FIG. 6 is a graph of data from PCR amplification of electrophoresed WBCs.
Figure 7:
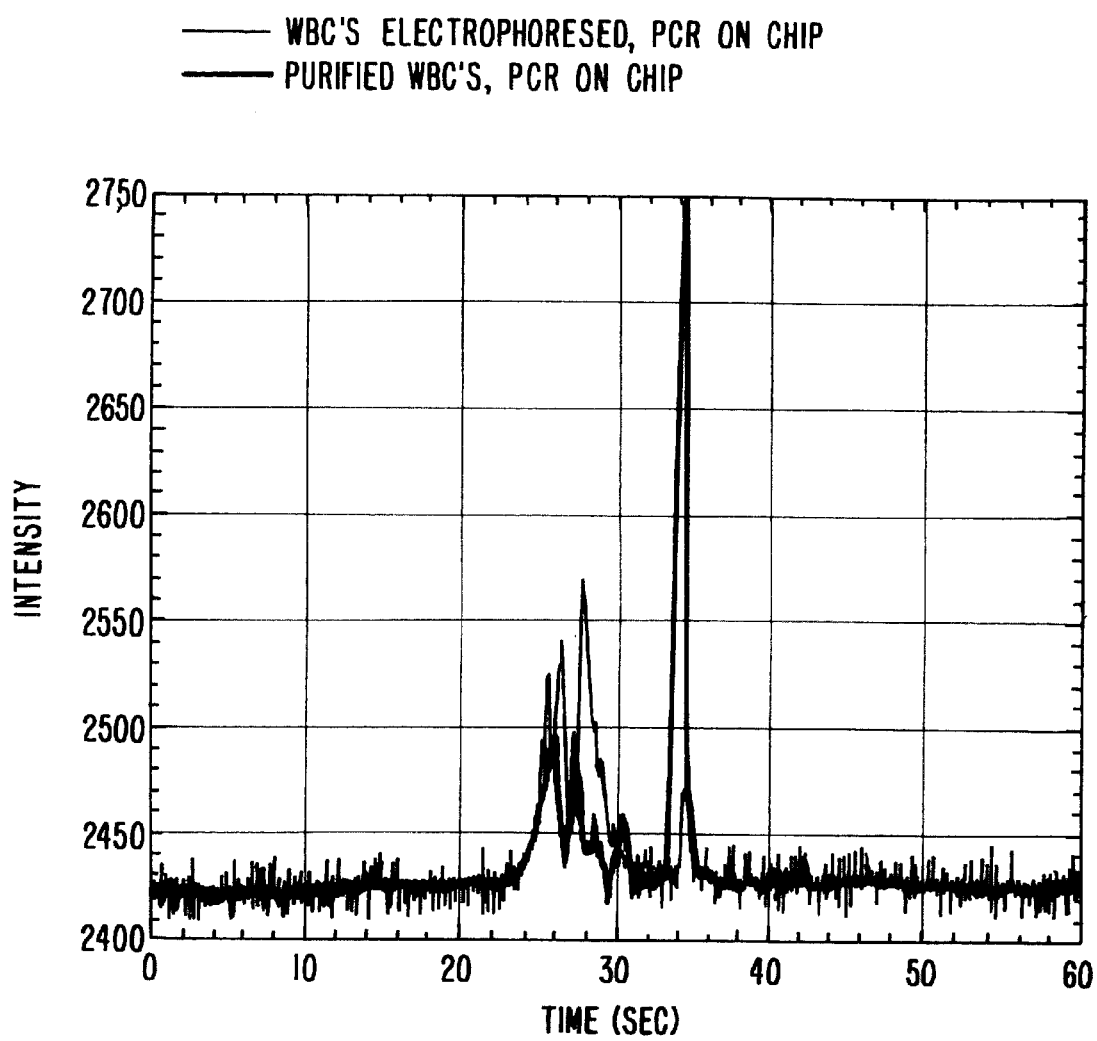
FIG. 7 is a graph of data from PCR amplification of electrophoresed WBCs and PCR amplification of purified WBCs.

The third experiment also used the 12A chip but with all channels filled and remaining filled with sieving gel. In addition, the two wells at the ends of the separation channel were filled with gel. For the first part of the experiment, approximately 2000 lymphocytes (white blood cells) purified from whole blood in a conventional way (centrifugation) were added to 20 $\mu$L of PCR reaction mix and placed in the sample well of the chip. The wells were overlaid with mineral oil and the chip was cycled using a thermocycler. After cycling, the PCR product was separated on a different but still cycled 12A chip. FIG. 5 shows the electropherogram for this portion where the amplified peak of the HLA locus (about 300 bp) is seen at around 34 seconds at the same time as the 270–310 bp fragments in the PhiX 174 standard ladder. For the second part of the experiment, PCR reaction mix without DNA template was placed in the sample well of a fresh chip and 5% whole blood in which the red blood cells had been lysed was placed in another well. Lymphocytes (white blood cells) were electrophoresed through the channel to the well containing the PCR reaction mixture until 20–100 lymphocytes were in the PCR well. The chip was cycled and DNA separated as for the previous chip. This is shown in FIG. 6. Amplification was achieved for both purified and electrophoresed lymphocytes, although the amount of product for purified lymphocytes was larger than for electrophoresed lymphocytes as shown in FIG. 7 in which the two product peaks are overlaid. Sufficient PCR cycles were run to ensure that the reaction had reached a plateau stage, because the number of starting copies was different.

These experiments demonstrated the ability to integrate several steps of a complex biochemical assay in a multiphasic microchip format.

Example 2
PCR Compatibility with Separations Gel

A simplified chip for PCR/DNA separation using joule heating for PCR includes a continuous fluid phase throughout the chip such that PCR amplification is carried out in one section of the chip by joule heating and DNA separation is performed in another. This example shows that the polymerase chain reaction (PCR) can be run in the presence of a DNA separations gel in a microfluidic system, and that the resulting nucleic acid DNA products are separable in the gel in a microfluidic system.

In this example, the 12 A chip described above was filled with one of 5 media comprising PCR reaction reagents. The 5 media which were tested are: 1.7% Agarose; 5% linear polyacrylamide (PA); 0.5% Methyl cellulose; 2.5% polyethylene oxide (PEO), and 0.5% hydroxy cellulose (HEC). Solutions containing the separation media were prepared in diH$_2$O such that the final concentration in the PCR mixture was the appropriate concentration for DNA separation:

| Sieving medium | Final Concentration | g/mL DNA |
|---|---|---|
| agarose | 1.7% | 0.45 |
| Linear PA | 5% | .131 |
| Methyl cellulose | 0.5% | .013 |
| PEO | 2.5% | .065 |
| HEC | 0.5% | .013 |

The PCR master mix was prepared as follows:
H$_2$O+sieving matrix 36.3 $\mu$L
buffer 10 $\mu$L
dNTPs 10 $\mu$L
triton 10 $\mu$L
BSA 10 $\mu$L
MgCl$_2$ 10 $\mu$L
HLA P1 3 $\mu$L
HLA P2 3 $\mu$L
1/10 YP 1 $\mu$L
UNG 1 $\mu$L
Taq gold 0.7 $\mu$L The positive control for PCR was 47.5 $\mu$L of the above master mix with 2.5 $\mu$L 1 ×DNA. The negative control was 47.5 $\mu$L of the above master mix with 2.5 $\mu$L H$_2$O (both cycled in standard PCR tubes). PCR reaction conditions were at 94° C. (15 minutes); 94° C. (30 seconds); 55° C. (30 seconds); 65° C. (60 seconds). Results showed that PCR amplification was successful in the presence of each of the sieving matrices described above (PEO and HEC were slightly inhibitory).

Once PCR in the presence of the various sieving matrixes was shown to be possible, separation of the PCR fragments in the sieving matrix in 1×PCR buffer was investigated on the 12 A chip. The PCR mixture was amplified in the presence of 0.5% MC. The 0.5% MC sieving matrix was dispersed throughout the 12 A chip discussed above. PCR products and phi X control DNA were separated in the channels of the 12 A chip, by applying current to wells as described below:

| Script 1 | well number 2 | 7 | 8 | time |
|---|---|---|---|---|
| −1.3 $\mu$A | 2000 v | −1.3 $\mu$A | −6 $\mu$A | 45 sec |
| 1000 v | 4 $\mu$A | 2000 v | 4 $\mu$A | 1 sec |
| 500 v | 0.5 $\mu$A | 10 $\mu$A | 0.5 $\mu$A | 180 sec |

Figure 8:
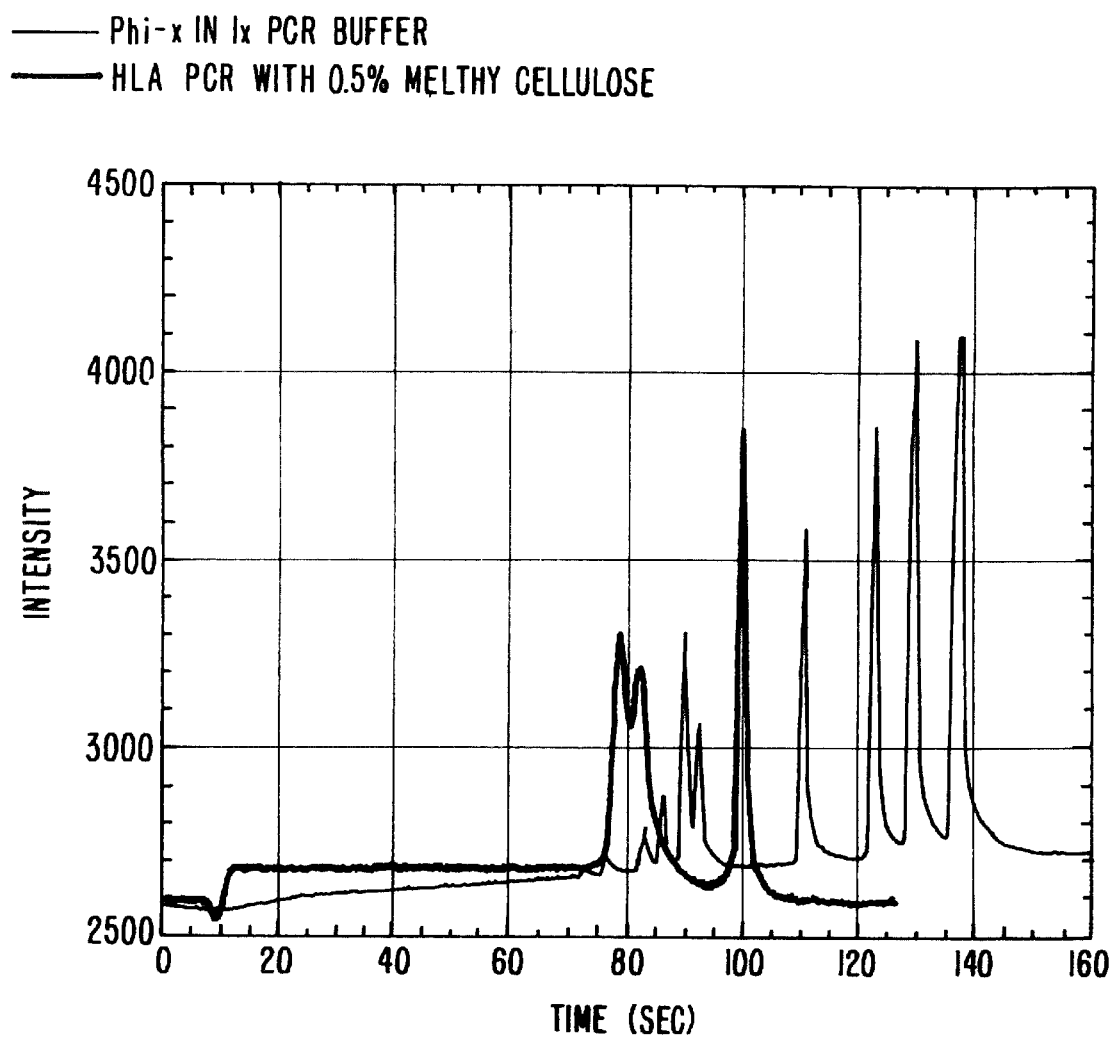
FIG. 8 is a graph of HLA PCR with 0.5% methylcellulose.

The phi X control was 2.5 $\mu$L phi-X DNA (i.e., Phi-X 174 digested to completion with Hae III, available from Promega) with 1 $\mu$L 1/100 sybergreen and 10 $\mu$L 10×PCR buffer, plus 86.5 $\mu$L H$_2$O. FIG. 8 shows the epifluorescent profile of the PCR product and phi X control. Intensity units are arbitrary. As shown, PCR products made in the presence of 0.5% methyl cellulose were resolved in channels as described.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method of performing a polymerase chain reaction in a microfluidic apparatus, said method comprising:

providing a microfluidic device comprising at least two intersecting channels in fluid communication;

filling at least one of said two intersecting channels with an electrophoretic phase selected from the group consisting of a sieving matrix and a molecular partition matrix, wherein the electrophoretic phase comprise at least two PCR reactants and a thermostable polymerase dispersed therein;

performing the polymerase chain reaction in the presence of the electrophoretic phase to produce at least a first product.

2. The method of claim 1, said method further comprising a step of separating the at least first product from the reactants in the presence of the electrophoretic phase.

3. The method of claim 1, wherein at least one of said intersecting channels comprise a reaction region.

4. The method of claim 1, wherein the microfluidic device comprises a high-resistance channel region for heating the at least two PCR reactants.

5. The method of claim 1, wherein the two PCR reactants are heterogeneously dispersed throughout at least a portion of the electrophoretic phase.

6. The method of claim 1, wherein the two PCR reactants are homogeneously dispersed throughout at least a portion of the electrophoretic phase.

7. The method of claim 1, wherein at least one of the two PCR reactants is heterogeneously dispersed in at least a portion of the electrophoretic phase and one of the two PCR reactants is homogeneously dispersed throughout the electrophoretic phase.

8. A method of performing a polymerase chain reaction in a microfluidic apparatus, said method comprising:

providing a microfluidic device comprising at least two intersecting channels in fluid communication;

filling at least one of said two intersecting channels with a mixture comprising a sieving matrix, a thermostable polymerase and a plurality of PCR reaction components;

performing the PCR in the presence of the sieving matrix to produce at least a first product.

9. The method of claim 8, said method further comprising a step of separating the at least first product from the PCR reaction components in the presence of the sieving matrix.

10. The method of claim 8, wherein the step of separating is carried out in a channel region different from a channel region for performing the PCR.

11. The method of claim 8, wherein the sieving matrix is selected from a group consisting of agarose, linear polyacrylamide, methylcellulose, polyethylene oxide and hydroxy ethyl cellulose.

12. The method of claim 8, wherein one of said at least two intersecting channels have an interior dimension of between about 0.1 $\mu$m and 500 $\mu$m.

13. The method of claim 8, wherein the two PCR reactants are heterogeneously dispersed throughout at least a portion of the sieving matrix.

14. The method of claim 8, wherein the two PCR reactants are homogeneously dispersed throughout at least a portion of the sieving matrix.

15. The method of claim 8, wherein at least one of the two PCR reactants is heterogeneously dispersed in at least a portion of the sieving matrix and one of the two PCR reactants is homogeneously dispersed throughout the sieving matrix.

16. The method of claim 8, wherein one of said at least two intersecting channels comprise a reaction region.

17. The method of claim 16, wherein the reaction region is substantially filled with the sieving matrix.

18. The method of claim 8, wherein one of said at least two intersecting channels comprise a separation region.

19. The method of claim 18, wherein the separation region is substantially filled with the sieving matrix.

* * * * *